US009068979B2

United States Patent
Fukushima et al.

(10) Patent No.: US 9,068,979 B2
(45) Date of Patent: Jun. 30, 2015

(54) MICRO BIO SENSOR AND METHOD FOR MANUFACTURING THE MICRO BIO SENSOR

(75) Inventors: Hitoshi Fukushima, Suwa (JP); Akira Nishimura, Hyogo (JP); Mitsuhiro Ban, Hyogo (JP); Asahi Yamazaki, Hyogo (JP); Takuya Asai, Hyogo (JP)

(73) Assignee: Seiko Epson Corporation (JP)

( * ) Notice: Subject to any disclaimer, the term of this patent is extended or adjusted under 35 U.S.C. 154(b) by 1312 days.

(21) Appl. No.: 12/123,519

(22) Filed: May 20, 2008

(65) Prior Publication Data

US 2009/0081766 A1   Mar. 26, 2009

(30) Foreign Application Priority Data

May 21, 2007   (JP) .................. 2007-134688

(51) Int. Cl.
*C12M 1/34* (2006.01)
*G01N 33/543* (2006.01)
(Continued)

(52) U.S. Cl.
CPC .... *G01N 33/54353* (2013.01); *G01N 33/56911* (2013.01); *G01N 2015/1486* (2013.01); *G01N 2610/00* (2013.01)

(58) Field of Classification Search
CPC .................. G01N 33/54366; G01N 33/54373; B01J 2219/00722; B01J 19/0046; B01J 2219/00659; B82Y 30/00; B01L 7/52; B01L 2300/0636; C40B 40/06
USPC ............. 435/287.2, 6.11, 6.12, 177; 438/478; 205/777; 422/502
See application file for complete search history.

(56) References Cited

U.S. PATENT DOCUMENTS 3,992,371 A * 11/1976 Tobiki et al. .................. 540/330
4,789,804 A   12/1988 Karube et al.
7,402,381 B2   7/2008 Takiguchi et al.
(Continued)

FOREIGN PATENT DOCUMENTS

JP   62-64934   3/1987
JP   06-226090   8/1994
(Continued)

OTHER PUBLICATIONS

Dreesen, Laurent, Christophe Silien, Cedric Volcke, Yannick Sartenaer, Paul A. Thiry, Andre Peremans, Jerome Grugier, Jacquelin Marchand-Brynaert, Alain Brans, Stana Grubisic and Bernard Joris. "Adsorption Properties of teh Penicillin Derivative DTPA on Gold Substrates". ChemPhysChem. 2007, vol. 8, pp. 1071-1076. Wiley InterScience.*

(Continued)

*Primary Examiner* — Michael Hobbs
(74) *Attorney, Agent, or Firm* — Harness, Dickey & Pierce, P.L.C.

(57) ABSTRACT

A micro bio sensor which detects a microbe existing in a specimen is provided. The microbial sensor includes a base, a detector formed on the base, and a reaction layer formed on the detector, wherein the reaction layer is comprised of a self-assembled monolayer which is formed on the detector and an antibiotic which is immobilized through the self-assembled monolayer on the detector. By using the micro bio sensor, it is possible to detect species of the microbe concurrently and improve sensitivity for detecting the species of the microbe. Further, a method for manufacturing such a micro bio sensor is also provided.

10 Claims, 8 Drawing Sheets

(51) Int. Cl.
*G01N 33/569* (2006.01)
*G01N 15/14* (2006.01)

(56) References Cited

U.S. PATENT DOCUMENTS

| | | | | |
|---|---|---|---|---|
| 2001/0021534 | A1* | 9/2001 | Wohlstadter et al. | 436/518 |
| 2005/0003560 | A1* | 1/2005 | Zeng et al. | 436/527 |
| 2006/0196779 | A1* | 9/2006 | Fukushima et al. | 205/792 |

FOREIGN PATENT DOCUMENTS

| | | |
|---|---|---|
| JP | 11-165066 | 6/1999 |
| JP | 2000-065708 | 3/2000 |
| JP | 2002-181371 | 6/2002 |
| JP | 2002-340766 | 11/2002 |
| JP | 2005-084028 | 3/2005 |
| JP | 2005-172680 | 6/2005 |

OTHER PUBLICATIONS

Davis, Frank, Seamus P.J. Higson. "Structured thin films as functional components within biossensors". Biosensors and Bioelectronics. 21 (2005) 1-20. Elsevier.*

Toby, A. A. Jenkines, Neville Boden, Richard J. Bushby, Stephen D. Evans, Peter F. Knowles, Robert E. Miles, Simon D. Ogier, Holger Schoenherr and G. Julius Vancso. "Microcontact printing of Lipophilic Self-Assembled Monolayers for the Attachment of Biomimetic Lipid Bilayers to Surfaces". J. Am. Chem. Soc. 1999, 121, 5274-5280. ACS.*

"Surface Grafted Antibodies: Controlled Architecture Permits Enhanced Antigen Detection", Langmuir, vol. 21, No. 24 (2005), p. 10907-10911.

* cited by examiner

MICRO BIO SENSOR AND METHOD FOR MANUFACTURING THE MICRO BIO SENSOR

BACKGROUND

1. Technical Field

The present invention relates to a micro bio sensor and a method for manufacturing the micro bio sensor.

2. Related Art

In a field such as foods and drinks, drugs and medicines, and cosmetics, species of a microbe are identified and a total number of the species of the microbe is counted for the purpose of determining whether or not microbial contamination occurs.

As a conventional method for counting a total number of species of a microbe, for example hiochi bacterium, contained in a specimen, the following method is carried out. After a solution containing the microbe (hiochi bacterium) is added in a agar medium and then the agar medium is cultivated for a few days, a number of colonies produced in the agar medium is counted by a visual check or with a colony counter. And thereafter, the total number of the hiochi bacterium contained in the specimen is obtained by counting backward using the counted number of the colonies.

Further, for identifying species of a microbe, the following method is generally carried out. Namely, the method is carried out by preparing a medium which contains an additive that develops a predetermined color if colonies of a predetermined microbe are produced in an agar medium, adding a solution containing an unknown microbe to the medium, cultivating the medium for a few days, and identifying the microbe based on the developed color of the additive.

However, in the conventional methods for cultivating the microbe by using the agar medium, a considerably long time e.g. 24 to 120 hours is required for the cultivation. Further, various skills are required in preparing the medium, preparing the solution containing the unknown microbe, adding the solution containing the unknown microbe to the medium, studying cultural conditions, counting colonies and the like. Therefore, it is desired to develop a new method that can detect or measure a microbe more rapidly and easily than the conventional methods.

Under the circumstances, recently, there are proposed a detecting method using an electrochemical reaction or a gene, methods using an immune reaction or an emission of ATP and the like in order to identify a microbe.

However, in the detecting method using the electrochemical reaction or the gene, the methods using the immune reaction or the emission of ATP and the like, various skills are still required in pre-cultivation of the microbe or handling thereof. Further, these methods have problems such as detection sensitivity of the microbe, price of an apparatus to be used in these methods and the like. Therefore, these methods do not replace the conventional methods for cultivating the microbe using the agar medium as described above.

For these reasons, it is strongly desired to develop a method and a principle that are capable of detecting a microbe easily with a high sensitive for accomplishing high quality control of alcoholic beverages.

On the other hand, in a method for detecting a microbe based on changes in frequency that are caused by bonding the microbe to a surface of an electrode in a state that a voltage is applied between two electrodes, a method using a crystal oscillator in which an antimicrobial antibody is immobilized on a surface of an electrode is proposed. And one example thereof is disclosed in JP-A-62-64934. However, the method is not put into practical use due to low detection sensitivity to the microbe.

Further, a crystal oscillator-micro bio sensor in which an antimicrobial antibody is immobilized through protein A or protein G on a surface of an electrode for the purpose of improving detection sensitivity is proposed as disclosed in JP-A-2002-340766. This sensor is not appropriate in the purpose of detecting two or more species of a microbe concurrently.

Furthermore, a rapid detection device for detecting a microbe is proposed as disclosed in JP-A-2005-172680. The rapid detection device is provided with a base material comprised of substances that can specifically trap a desired microbe existing in a specimen. And the rapid detection device includes a means for optically detecting the desired microbe trapped on the base material. This device is also not appropriate in the purpose of detecting two or more species of the microbe concurrently.

SUMMARY

Accordingly, it is an object of the present invention to provide a micro bio sensor which can detect species of a microbe concurrently with high sensitivity. Further, it is also an object of the present invention to provide a method for manufacturing such a micro bio sensor.

These objects are achieved by the present invention described below.

In a first aspect of the present invention, there is provided a micro bio sensor which detects a microbe existing in a specimen, the micro bio sensor comprising a base, a detector formed on the base, a reaction layer formed on the detector, wherein the reaction layer is comprised of a self-assembled monolayer which is formed on the detector and an antibiotic which is immobilized through the self-assembled monolayer on the detector.

According to the micro bio sensor described above, since the microbe is bonded to the antibiotic contained in the reaction layer, it is possible to detect species of the microbe with high sensitivity.

In the micro bio sensor according to the present invention, it is preferred that the detector is comprised of a first electrode having one surface and the other surface, a second electrode and a third electrode, and the first electrode is arranged in a side by side relation between the second electrode and the third electrode.

According to the micro bio sensor described above, since the microbe is detected by using the three electrodes, it is possible to detect the species of the microbe with high sensitivity.

In the micro bio sensor according to the present invention, it is also preferred that the self-assembled monolayer is comprised of molecules having one end and the other end, each molecule having a sulfide group, a disulfide group or a mercapto group at the one end thereof, and wherein the sulfide group, the disulfide group or the mercapto group is bonded to the one surface of the first electrode in the self-assembled monolayer.

According to the micro bio sensor described above, since the self-assembled monolayer can be formed on the surface of the first electrode efficiently, it is possible to immobilize the antibiotic on the surface of the first electrode through the self-assembled monolayer easily.

In the micro bio sensor according to the present invention, it is also preferred that the reaction layer is further comprised of streptavidin, and at least one of the molecules has at the other end thereof a biotin to be bonded to the streptavidin.

According to the micro bio sensor described above, it is possible to immobilize the antibiotic on the surface of the first electrode through the self-assembled monolayer efficiently.

In the micro bio sensor according to the present invention, it is also preferred that the reaction layer is further comprised of complex functional molecules having one end and the other end, and each complex functional molecule has at the one end thereof a carboxyl group, an amide group, an ether group, an ester group or a thioester group which is to be bonded to the antibiotic.

According to the micro bio sensor described above, it is possible to obtain the complex functional molecules to which the antibiotic is bonded reliably.

In the micro bio sensor according to the present invention, it is also preferred that the complex functional molecules contain a polymerizable group.

According to the micro bio sensor described above, since functionalized molecules can be bonded to the polymerizable group contained in the complex functional molecules, it is possible to detect the microbe with higher sensitivity.

In the micro bio sensor according to the present invention, it is also preferred that at least one of the complex functional molecules has at the other end thereof a biotin to be bonded to a streptavidin.

According to the micro bio sensor described above, since two complex functional molecules are bond to the streptavidin at the other end thereof, it is possible to detect the microbe with higher sensitivity.

In the micro bio sensor according to the present invention, it is also preferred that the antibiotic is constituted of an antimicrobial agent or an antivirus agent.

According to the micro bio sensor described above, it is possible to detect a bacterium or a virus with high sensitivity.

In the micro bio sensor according to the present invention, it is also preferred that the antimicrobial agent is constituted of a beta-lactam antibiotic.

According to the micro bio sensor described above, since the antibiotic is bonded to the bacterium efficiently, it is possible to detect species of the bacterium with high sensitivity.

In the micro bio sensor according to the present invention, it is also preferred that the beta-lactam antibiotic is constituted of penicillin.

According to the micro bio sensor described above, since the antibiotic is bonded to the bacterium more efficiently, it is possible to detect species of the bacterium with higher sensitivity.

In the micro bio sensor according to the present invention, it is also preferred that the microbe is detected by the first and second electrodes in a state that a voltage is applied between the first electrode and the second electrode to obtain an impedance of an electrical current flowing between the first and second electrodes, wherein when the microbe existing in the specimen is bonded to the antibiotic contained in the reaction layer, the impedance is changed due to the bonding between the antibiotic and the microbe.

According to the micro bio sensor described above, it is possible to detect the species of the microbe easily, rapidly and high sensitively.

In the micro bio sensor according to the present invention, it is also preferred that the detector is comprised of a first electrode having one surface and the other surface, a second electrode formed on the base and a piezoelectric layer formed vertically between the other surface of the first electrode and the second electrode, and the detector is configured to oscillate in a predetermined frequency.

According to the micro bio sensor described above, since the microbe is detected based on changes of the frequency generated by the piezoelectric layer, it is possible to detect the species of the microbe high sensitively and easily.

In the micro bio sensor according to the present invention, it is also preferred that the microbe is detected by the detector in a state that a voltage is applied between the first electrode and the second electrode, wherein when the microbe existing in the specimen is bonded to the antibiotic contained in the reaction layer, the predetermined frequency is changed due to the bonding between the antibiotic and the microbe.

According to the micro bio sensor described above, it is possible to detect species of the microbe easily and rapidly with high sensitivity.

In a second aspect of the present invention, there is provided a method for manufacturing a micro bio sensor which comprises preparing a base, forming a detector on the base, and forming a reaction layer on the detector to obtain the micro bio sensor, wherein forming the reaction layer on the detector comprises preparing complex functional molecules each having an antibiotic, forming a self-assembled monolayer comprised of molecules having one end and the other end on the detector and immobilizing the complex functional molecules having the antibiotic through the self-assembled monolayer on the detector.

According to the manufacturing method described above, since the sensor is manufactured by using a few steps as described above, it is possible to obtain the micro bio sensor easily and rapidly.

In the manufacturing method according to the present invention, it is preferred that the complex functional molecules have one end and the other end, and at least one of the complex functional molecules has at the one end thereof a biotin.

According to the manufacturing method described above, it is possible to bond the biotin to a streptavidin firmly when the self-assembled monolayer is subjected to a treatment using the streptavidin.

In the manufacturing method according to the present invention, it is also preferred that at least one of the molecules of the self-assembled monolayer has at the one end thereof a biotin, and wherein forming the reaction layer on the detector further comprises subjecting the self-assembled monolayer to a streptavidin treatment before immobilizing the complex functional molecules through the self-assembled monolayer on the detector.

According to the manufacturing described above, since the streptavidin bonded to the molecules at the one end thereof in the self-assemble monolayer is bonded to the biotin of the complex functional molecules firmly, it is possible to obtain the micro bio sensor that can be operated stably.

DESCRIPTION OF EXEMPLARY EMBODIMENTS

Hereinbelow, with reference to the accompanying drawings, preferred embodiments of a micro bio sensor and a method for manufacturing a micro bio sensor according to the invention will be described in details.

First Embodiment

1 Micro Bio Sensor

Figure 1:
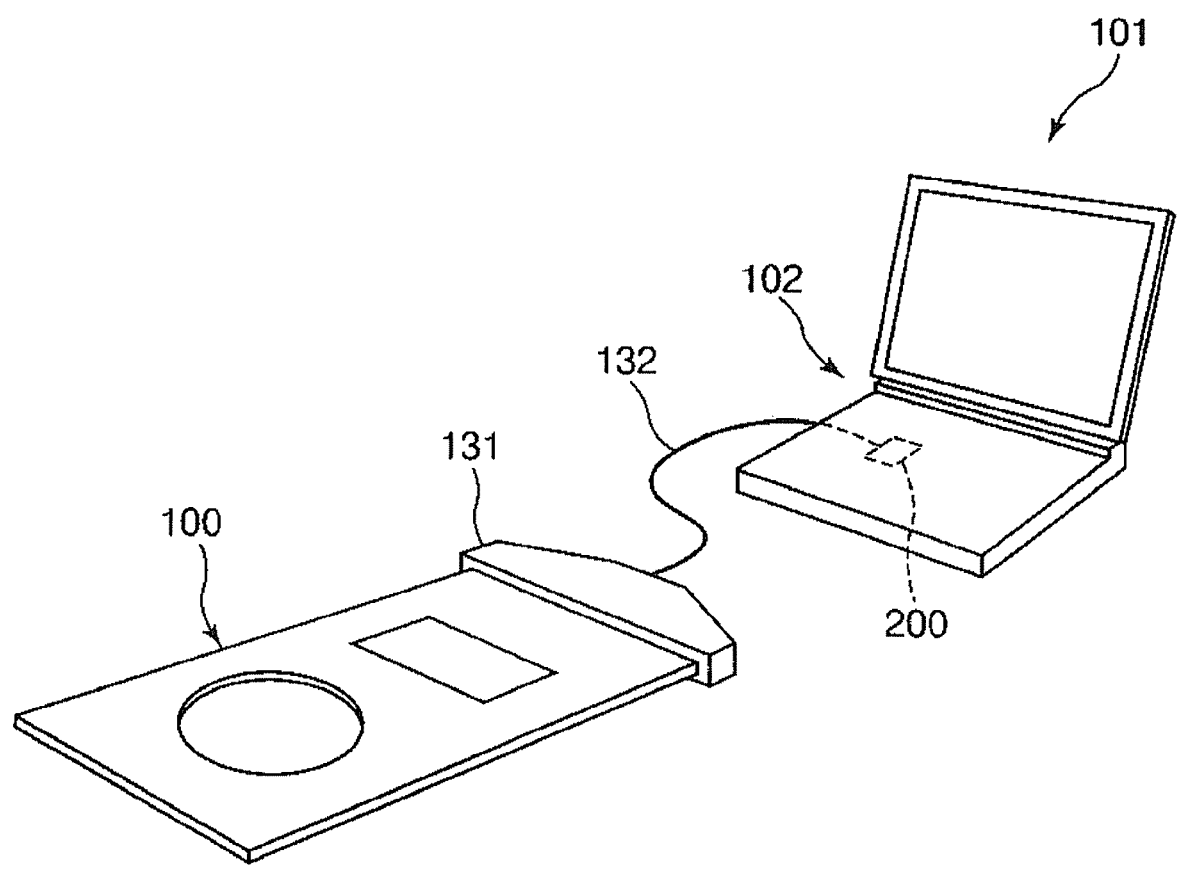
FIG. 1 is a perspective view which shows a state that a micro bio sensor in accordance with the present invention is attached to a measurement device.
Figure 2:
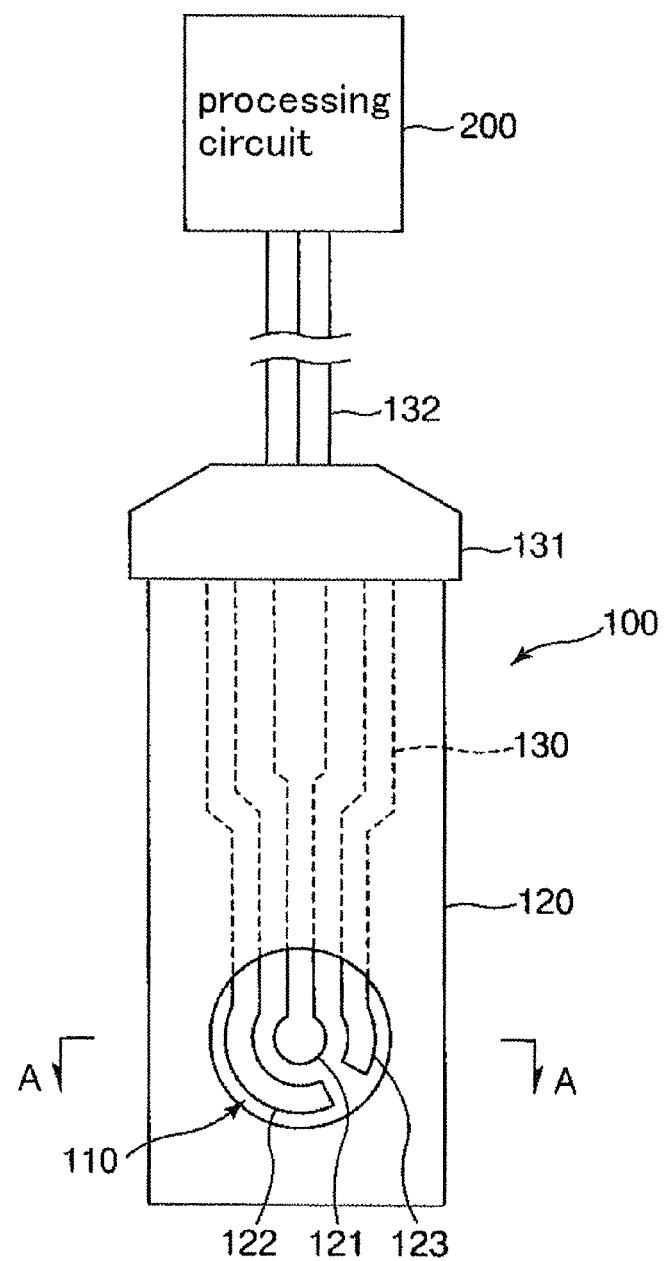
FIG. 2 is a plan view which schematically shows the micro bio sensor shown in FIG. 1.
Figure 3:
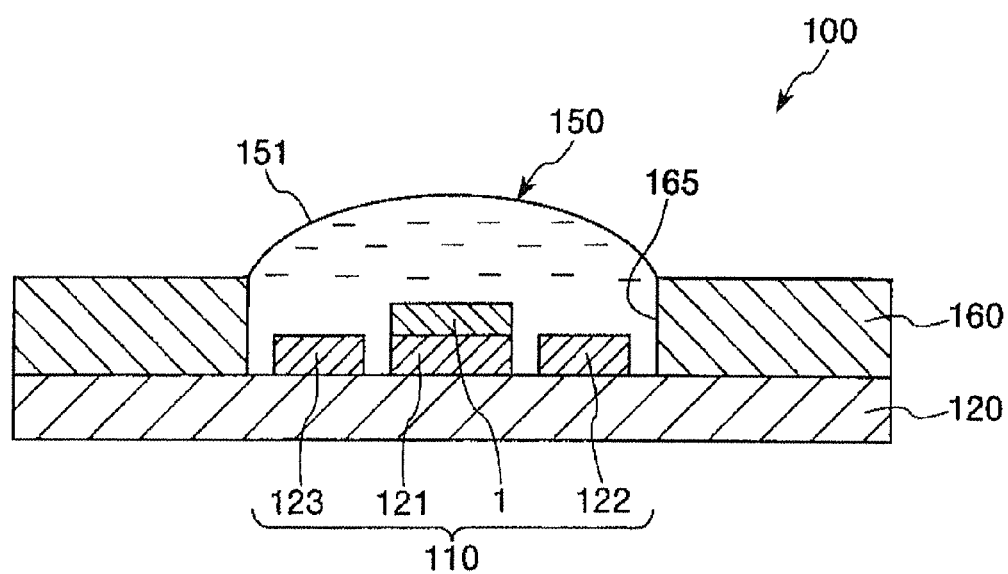
FIG. 3 is a vertical sectional view taken along line A-A in FIG. 2, which shows the micro bio sensor shown in FIG. 2.
Figure 4:
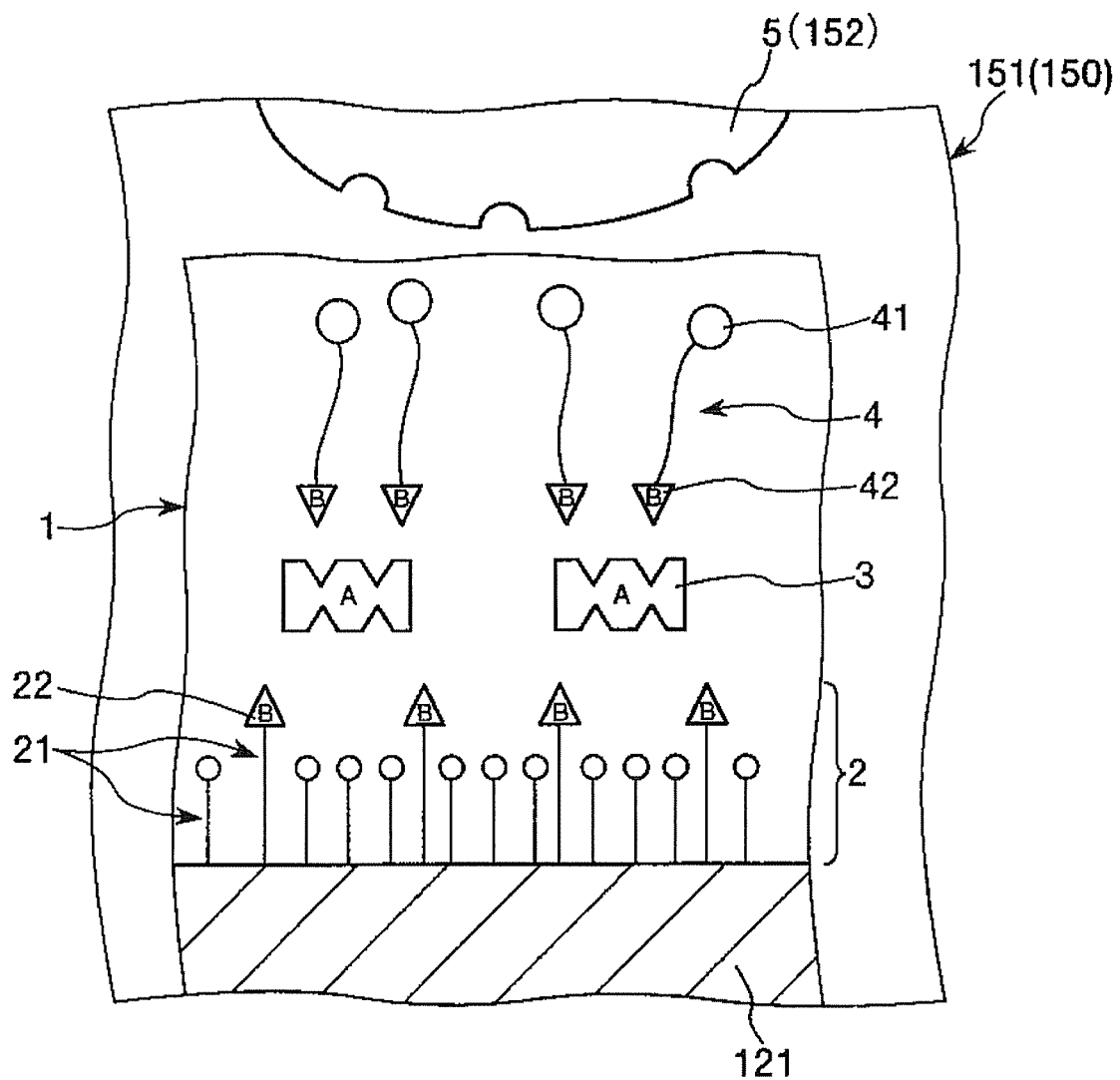
FIG. 4 is an enlarged view of a part of the vertical sectional view taken along line A-A shown in FIG. 3.

FIG. 1 is a schematic view (perspective view) which shows a state that a micro bio sensor in accordance with the present invention is attached to a measurement device. FIG. 2 is a plan view which schematically shows the micro bio sensor shown in FIG. 1. FIG. 3 is a vertical sectional view taken along line A-A in FIG. 2, which shows the micro bio sensor shown in FIG. 2. FIG. 4 is an enlarged view of a part of the vertical sectional view taken along line A-A shown in FIG. 3.

In the following description, the front side of the sheet of FIG. 2 will be referred to as "upper" and the back side thereof will be referred to as "lower". Further, the upper side in each of FIG. 3 and FIG. 4 will be referred to as "upper" and the lower side thereof will be referred to as "lower".

A measurement device (electronic device) 101 shown in FIG. 1 includes a micro bio sensor 100, an arithmetic device (computing device) 102 provided with a processing circuit 200 which analyzes an electrical current value (impedance) obtained by using the micro bio sensor 100, a connector 131 for attaching the micro bio sensor 100, and a wire 132 for connecting the processing circuit 200 to the connector 131.

The micro bio sensor 100 is provided with a detection section 110 including a work electrode 121, an opposite electrode 122 and a reference electrode 123 which are formed on a base 120 as shown in FIGS. 2 and 3. The detection section 110 also includes a reaction layer 1 formed on the work electrode 121 as shown in FIG. 3. The micro bio sensor 100 is also provided with wires 130 for connection between each of the work electrode 121, the opposite electrode 122 and the reference electrode 123 and the connector 131 on the base 120 as shown in FIG. 2. In the detection section 110, the work electrode 121 is arranged in a side by side relation between the opposite electrode 121 and the reference electrode 123 on the base 120.

The work electrode 121, the opposite electrode 122 and the reference electrode 123 are electrically connected to the processing circuit 200 through the wires 130, the connector 131 and the wire 132, respectively. Further, the micro bio sensor 100 is removable with respect to the connector 131.

As shown in FIG. 3, an upper surface of the base 120 other than the detection section 110 is covered with an insulation film 160. In other words, the insulation film 160 is formed on the upper surface of the base 120 other than the detection section 110 so as to cover the wires 130. The detection section 110 is exposed from an opening portion 165 which is formed in a part of the insulation film 160 at a position corresponding to the detection section 110.

Such a micro bio sensor 100 can be used as follows. As shown in FIG. 3, a liquid sample 151 is supplied into a sample supply space 150 partitioned by the base 120 and the insulation film 160 (namely opening portion 165) so that the liquid sample 151 comes into contact with the reaction layer 1 formed on the work electrode 121 as described later. And then in a state that a voltage is applied between the work electrode 121 and the opposite electrode 122, if a microbe 152 exists in the liquid sample, the microbe 152 contained in the liquid sample 151 is reacted (bonded) with an antibiotic 41 contained in the reaction layer 1 as shown in FIG. 4.

This makes it possible to change impedance of an electrical current flowing between the work electrode 121 and the opposite electrode 122. In this way, it is possible to detect presence of the microbe 152 contained in the liquid sample 151 based on changes in the impedance which is obtained from values of the electrical current, the changed electrical current and the applied voltage. Further, it is also possible to determine quantity of the microbe 152 contained in the liquid sample 151 as described later.

In this regard, examples of such a liquid sample (specimen) 151 include: a body fluid such as blood, urine, sweat, lymph, spinal fluid, bile and saliva; a treated liquid obtained by subjecting such a body fluid to various treatments; a beverage such as soft drinks and alcoholic drinks; drugs and medicines; cosmetics; and the like.

Further, the microbe 152 contained in the liquid sample 151 is reacted with the antibiotic 41 as described later on a cell surface 5 of the microbe 152, thereby bonding to the antibiotic 41.

Examples of such a microbe 152 include: a bacterium such as lactic acid bacterium, hiochi bacterium and staphylococcus; a virus such as influenza virus and norovirus; a fungus such as yeast and mold; and the like.

The base 120 supports various parts mentioned above to constitute the micro bio sensor 100 and insulates the work electrode 121, the opposite electrode 122, the reference electrode 123 and the wires 130 as described above, respectively.

Examples of a constituent material of the base 120 include: various resin materials such as polyethylene, polypropylene, polystyrene, polyethylene terephthalate (PET), polyethylene naphthalate (PES) and polyimide (PI); various glass materials such as quartz glass; various ceramic materials such as alumina and zirconia; and the like. These materials may be used singly or in combination of two or more of them.

Examples of a constituent material of the work electrode 121 include: a metal material such as gold, silver, copper, platinum and alloys containing two or more of them; a metal oxide based material such as ITO (Indium Tin Oxide); a carbon based material such as graphite; and the like. Among these materials mentioned above, the constituent material is preferably the metal material, and more preferably gold or silver.

Since use of gold or silver as the constituent material of the work electrode 121 makes it possible to easily form the self-assembled monolayer 2 only by being in contact with organic molecules 21 constituting the self-assembled monolayer 2 as described later, it is possible to manufacture the micro bio sensor 100 more easily.

The reaction layer 1 is formed on the work electrode 121. As shown in FIG. 3, the upper surface and side surfaces of the reaction layer 1 are exposed in the sample supply space 150. Therefore, by supplying the liquid sample 151 to the sample supply space 150, it is possible to have the liquid sample 151 make contact with the reaction layer 1.

The opposite electrode 122 is an electrode which applies a voltage between the work electrode 121 and the opposite electrode 122. In a state that the liquid sample 151 is supplied to the sample supply space 150, if the voltage is applied between the opposite electrode 122 and the work electrode 121 so that potential of the work electrode 121 becomes higher than potential of the opposite electrode 122, impedance of the electrical current flowing between the work electrode 121 and the opposite electrode 122 is changed due to the bonding between the antibiotic 41 and the microbe 152.

In other words, electrical property of the reaction layer 1 is changed due to the bonding between the antibiotic 41 and the microbe 152. Therefore, it is possible to detect presence of the microbe 152 by observing changes in a value of the electrical current (electrical current value) reliably.

Examples of a constituent material of the opposite electrode 122 include same materials as those mentioned above as the constituent material of the work electrode 121.

A surface area of the opposite electrode 122 has a size preferably two times or more with respect to a surface area of the work electrode 121 in a state that no reaction layer is formed on the work electrode 121, and more preferably ten times or more. This makes it possible to measure the electrical current value with a high accuracy.

The reference electrode 123 is an electrode which applies a voltage between the opposite electrode 122 and the reference electrode 123. In a state that the liquid sample 151 is supplied into the sample supply space 150, the voltage is applied between the opposite electrode 122 and the reference electrode 123 to obtain a reference electrical current value.

The reference electrical current value which is obtained by applying the voltage between the opposite electrode 122 and the reference electrode 123 is compared with the electrical current value which is obtained by applying the voltage between the opposite electrode 122 and the work electrode 121. In this way, it is possible to obtain an accurate electrical current value (that is, impedance) changed by bonding between the microbe 152 and the antibiotic 41 with a high accuracy.

Examples of a constituent material of the reference electrode 123 include silver-silver chloride, mercury-mercury chloride and the like.

Further, each of the work electrode 121, the opposite electrode 122, the reference electrode 123 and the wires 130 as described above may be constituted of an assembly of a conductive material powder. This makes it possible to easily form the work electrode 121, the opposite electrode 122, the reference electrode 123 and the wires 130 by using various print processes. As a result, it is possible to simplify the manufacturing process of the micro bio sensor 100 greatly, thereby enabling the manufacturing cost of the micro bio sensor 100 to be reduced.

An average thickness of each of the work electrode 121, the opposite electrode 122 and the reference electrode 123 is not limited to any specific value but preferably in the range of 10 to 500 nm, and more preferably in the range of 50 to 300 nm.

As described above, the insulation film 160 has the opening portion 165 opening at the part corresponding to the detection section 110. And the sample supply space 150 is formed by the opening portion 165.

Such an insulation film 160 is constituted of an insulating material. Examples of such an insulating material, but not limited thereto, include an organic material, an inorganic material and the like.

Examples of the organic material that can be used as the insulating material include: a polymer compound such as polymethyl methacrylate, polyvinyl phenol, polyimide, polystyrene, polyvinyl alcohol and polyvinyl acetate; and the like. These materials may be used singly or in combination of two or more of them.

Examples of the inorganic material that can be used as the insulating material include: a metal oxide such as silicon oxide, aluminum oxide, tantalum oxide, zirconium oxide, cerium oxide, zinc oxide and cobalt oxide; a metal nitride such as silicon nitride, aluminum nitride, zirconium nitride, cerium nitride, zinc nitride, cobalt nitride, titanium nitride and tantalum nitride; a metal complex oxide such as barium strontium titanate and lead zirconium titanate; and the like. These materials may be used singly or in combination of two or more of them.

An average thickness of such an insulation film 160 is not limited to any specific value but is preferably in the range of about 10 to 5,000 nm, and more preferably in the range of about 50 to 1,000 nm. If the average thickness of the insulation film 160 falls within the above noted range, it is possible to reliably insulate the work electrode 121, the opposite electrode 122, the reference electrode 123 and the wires 130 to each other.

In the meantime, the micro bio sensor 100 of the present embodiment is a sensor which detects the microbe 152 existing in a specimen by bonding of the microbe 152 to the antibiotic 41 contained in the reaction layer 1 which is formed on the surface of the work electrode 121. In this micro bio sensor 100, the antibiotic 41 is immobilized through a self-assembled monolayer 2 on the surface of the work electrode 121, thereby constituting the reaction layer 1.

In other words, in the reaction layer 1 as shown in FIG. 4, the self-assembled monolayer 2 constituted of organic molecules 21 is formed on the surface of the work electrode 121. Each of the organic molecules 21 is bonded at a lower end thereof to the surface of the work electrode 121. And some organic molecules 21 have at an upper end thereof a biotin 22.

Further, streptavidins 3 are absorbed (bonded) to the biotins 22 of the organic molecules 21 in the self-assembled monolayer 2. That is to say, two biotins of the two organic molecules 21 are bonded to one sterptavidin 3 at a lower side of the streptavidin 3 as shown in FIG. 4.

Furthermore, each of complex functional molecules 4 is bonded at an upper end thereof to the antibiotic 41 and at a lower end thereof to biotin 42. And each of the biotins 42 is bonded to the streptavidin 3 at an upper side of the streptavidin 3. That is to say, two biotins 42 of the two complex functional molecules 4 are bonded to one sterptavidin 3 at an upper side of the streptavidin 3.

In this regard, it is to be noted that all of the complex functional molecules 4 are not necessary to be bonded at the lower end thereof to the biotins 42.

Hereinbelow, the relations among the respective substances and molecules will be described in detail.

The self-assembled monolayer 2 has functions of protecting the work electrode 121 and immobilizing (bonding) the antibiotic 41 to the surface of the work electrode 121. The self-assembled monolayer 2 is constituted of the organic molecules 21 each having a bond group which is to be bonded to the surface of the work electrode 121 as described above.

In the present embodiment, the bond group is constituted of a sulfide group but may be constituted of a disulfide group, a mercapto group and the like.

Examples of such organic molecules 21 include compounds (I) to (IV) represented by the following chemical structural formulas.

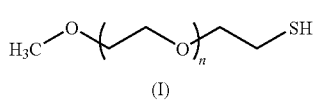

Compound (I)

In the chemical structural formula of the compound (I), n represents 1 to 15.

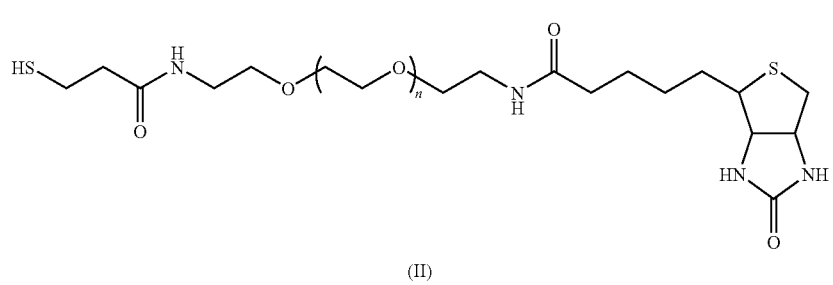

Compound (II)

In the chemical structural formula of the compound (II), n represents 1 to 15.

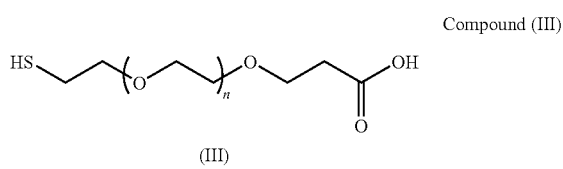

Compound (III)

In the chemical structural formula of the compound (III), n represents 1 to 15.

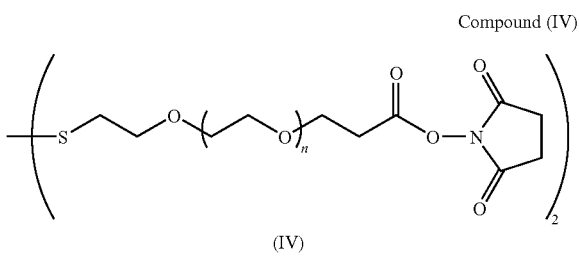

Compound (IV)

In the chemical structural formula of the compound (VI), n represents 1 to 15.

Among these compounds (I) to (IV) mentioned above, the organic molecules 21 are preferably the compounds (I) and (II) represented by the chemical structural formulas as described above.

Each of the compounds (I) and (II) has a mercapto group at one end of the chemical structure thereof. The mercapto group is reacted with a constituent material of the work electrode 121 easily, thereby forming a sulfide bond (metal-thiol bond). As a result, it is possible to bond the organic molecules 21 on the surface of the work electrode 121 easily and rapidly.

Further, the compound (II) has a biotin 22 at the other end of the chemical structure thereof. Therefore, if the self-assembled monolayer 2 is formed using the compound (II) and the biotin 22 of the compound (II) is subjected to a streptavidin 3 treatment, two biotins 22 of the two compounds (II) constituting the self-assembled monolayer 2 are bonded to one streptavidin 3.

Since streptavidin can generally be bonded to four biotins, the two biotins 42 bonded at the lower ends of the two complex functional molecules 4 can be bonded to the one streptavidin 3 as shown in FIG. 4. As a result, since two complex functional molecules 4 each having the antibiotic 41 at the upper end thereof is bonded to the one streptavidin 3 through the biotins 42. In this way, it is possible to improve detection sensitivity of the micro bio sensor 100.

The compound (III) represented by the chemical structural formula as described above has a carboxyl group at one end of the chemical structure thereof. Further, the compound (IV) represented by the chemical structural formula as described above has two succinimides at one end of the chemical structure thereof. Therefore, in the case where the self-assembled monolayer 2 is formed by using these compounds (III) and (IV), the antibiotic 41, particularly penicillin, can be directly bonded to the carboxyl group of the compound (III) (organic molecules 21) or the two succinimides of the compound (IV) (organic molecules 21) due to high reaction property thereof.

By bonding the organic molecules 21 of the compounds (I) to (IV) as described above to the surface of the work electrode 121, the self-assembled monolayer is formed on the work electrode 121 as shown in FIG. 4. In this regard, it is to be noted that "B" of the organic molecules 21 in FIG. 4 is referred to as a biotin 22 which is shown at the other end of the chemical structure of compound (II) as described above.

As described above, the streptavidin 3 is bonded (absorbed) to the biotins 22. Each of the biotins 22 is bonded to the upper end of the chemical structure of the compound (II) of the organic molecules 21 which constitute the self-assembled monolayer 2. Generally, it is known that one streptavidin is bonded to four biotins. In the present embodiment, the streptavidin 3 is bonded to two biotins 22 of the two compounds (II) of the organic molecules 21 on the lower side thereof and two biotins 42 of the two complex functional molecules 4 on the upper side thereof as shown in FIG. 4.

Therefore, two complex functional molecules 4 are bonded to one streptavidin 3 on the upper side thereof as shown in FIG. 4. As shown in FIG. 4, each of the complex functional molecules 4 has the antibiotic 41 and the biotin 42 at the opposite ends. Since each antibiotic 41 of the complex functional molecules 4 is bonded to the microbe 152, it is possible to detect the microbe 152 using the micro bio sensor 100 in which the complex functional molecules 4 are immobilized to the surface of the work electrode 121 through the streptavidin 3 and the self-assembled monolayer 2.

As described above, the antibiotic 41 is bonded to the cell surface 5 of the microbe 152 contained in the liquid sample 151. If the antibiotic 41 is bonded to the cell surface 5 of the microbe 152, an amount of electric charge in the reaction layer 1 is changed based on surface electricity and the like of the microbe 152. Therefore, the electrical current flowing in the reaction layer 1 is also changed by the bonding between the antibiotic 41 and the microbe 152. This also makes it possible to change impedance of the electrical current flowing in the reaction layer 1.

Such an antibiotic 41 may be selected depending on the species of microbe 152, but is not particularly limited as long as the antibiotic 41 can be bonded to the cell surface 5 of the microbe 152 which is a measuring object.

In the case where the microbe 152 is a bacterium, an antimicrobial agent can be used as the antibiotic 41. Examples of the antimicrobial agent that can be used as the antibiotic 41 include a beta-lactam antibiotic, a glycopeptides antibiotic and the like. Among these antimicrobial agents mentioned above, the beta-lactam antibiotic is preferably used as the antimicrobial agent.

In a peptidoglycan biosynthesis of a cell wall of a bacterium, if transpeptidase and carboxypeptidase work on a linear peptide glycan, terminal D-alanine of the linear peptide glycan leaves the linear peptide glycan and then cross-links are formed between the linear peptide glycans one after another. At this time, if the beta-lactam antibiotic is used in the peptidoglycan biosynthesis, the beta-lactam antibiotic works on the transpeptidase and the carboxypeptidase. As a result, it is possible to prevent the cross-links between the linear peptide glycans from being formed.

In other words, since a stereochemical structure of the beta-lactam antibiotic is similar to a stereochemical structure of D-alanylalanine of a peptidic terminus of the linear peptide glycan, the beta-lactam antibiotic is bonded to the transpeptidase and the carboxypeptidase. Therefore, active centers of the transpeptidase and the carboxypeptidase are acylated by the bonding. As a result, the transpeptidase and the carboxypeptidase are inactivated.

For these reasons, use of the beta-lactam antibiotic of the antibiotic 41 makes it possible to bond the antibiotic 41 to the cell wall of the bacterium efficiently. Therefore, the micro bio sensor 100 of the present invention, which has the reaction layer 1 containing such an antibiotic 41, can detect various bacteria (microbe 152) each having a cell wall existing in the liquid sample 151.

Examples of the beta-lactam antibiotic that can be used as antibiotic 41 include: a penicillin antibiotic such as benzylpenicillin (penicillin G), phenoxymethyl penicillin (penicillin V), penicillin N, penicillin O, methicillin, cloxacillin, ampicillin, amoxicillin, piperacillin, oxacillin, dicloxacillin, flucloxacillin, phenethicillin, propicillin, bacampicillin, talampicillin, temocillin, apalcillin, hetacillin, ciclacillin, carbenicillin, ticarcillin, mezlocillin, sultamicillin, azlocillin, bibmecillinam and sulbenicillin; a cephem antibiotic; cephalodine, cefapirin, cephaloridine, cefazolin, cephalexin, cefaladi, cefadroxil, cefamandole, cefonicid, ceforanide, cefaclor, cefixime, cefprozil, ceftriaxone, ceftazidime, cefoxitin, cefotaten, cefinetazole, cefuroxime, ceftizoxime, cefotaxime, cefbuperazone, cefminox, cefsulodin, cefoperazone, ceftibuten, cefetamet, cefepime, cefpirome, mecillinam, xalactam, nocardicin, sulfazecdine and the like.

Among these beta-lactam antibiotics mentioned above, the beta-lactam antibiotic is preferably the penicillin antibiotic, and more preferably the phenoxymethyl penicillin (penicillin V).

The penicillin antibiotic, particularly the penicillin V inhibits the activity of both the transpeptidase and the carboxypeptidase more strongly. Therefore, it is possible for the penicillin antibiotic to be bonded to various bacteria easily and firmly.

Further, in the case where the microbe 152 is a virus, an antivirus agent can be used as the antibiotic 41. Examples of the antivirus agent that can be used as the antibiotic 41 include a neuraminidase inhibitor, oseltamivir, oseltamivir phosphate, zanamivir, amantadine, rimantadine and the like.

Further, examples of the complex functional molecules 4 containing such an antimicrobial agent or an antivirus agent as the antibiotic 41 include compounds (V) and (VI) represented by the following chemical structural formulas.

Compound (V)

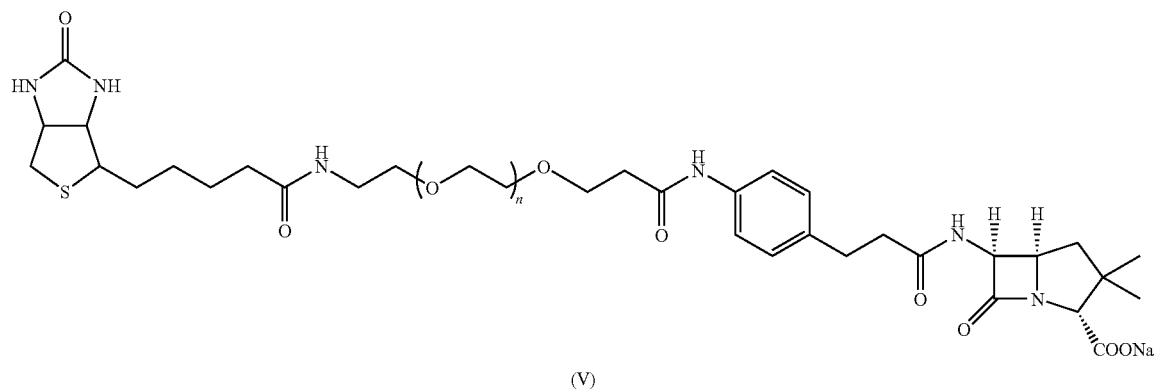

(V)

In the chemical structural formula of the compound (V), n represents 1 to 15.

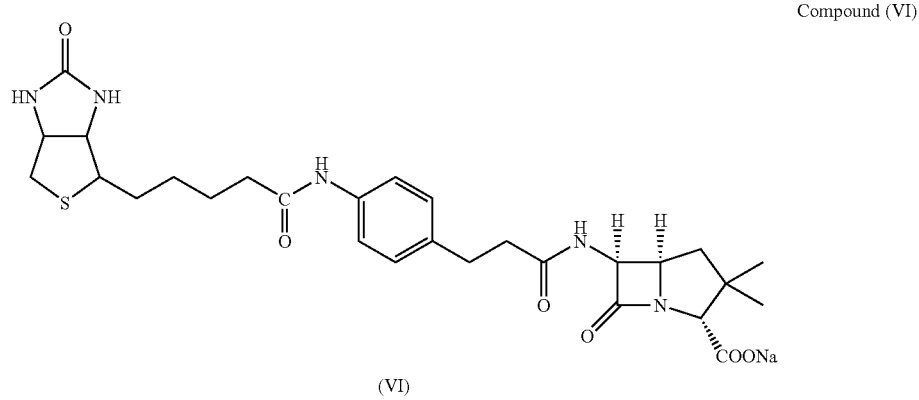

Compound (VI)

(VI)

Since in the compounds (V) and (VI) (complex functional molecules 4), the antibiotic (penicillin) 41 is bonded at one terminus thereof by an amido bond, it is possible to easily obtain the complex functional molecules 4 by a dehydration reaction between the penicillin in which an amino group is bonded at the ortho position of a benzene ring of the penicillin to the benzene ring thereof and a compound which has at the terminus thereof a carboxyl group.

Since the biotin 42 is bonded at the other terminus of each of the compounds (V) and (VI), the biotin 42 can be firmly bonded to the streptavidin 3 bonded to the organic molecules 21 with the same bonding strength as that of a covalent bond. As a result, it is possible to reliably immobilize the complex functional molecules 4 having the antibiotic 41 to the surface of the work electrode 121 through the streptavidin 3 and the self-assembled monolayer 2.

Further, since one streptavidin 3 can be bonded to two biotins 42 as shown in FIG. 4, it is possible to bond the two complex functional molecules 4 to the one streptavidin 3. As a result, it is possible to immobilize many complex functional molecules 4 to the surface of the work electrode 121 through the streptavidins 3 and the self-assembled monolayer 2. For this reason, it is possible to improve detection sensitivity of the micro bio sensor 100 to the microbe 152.

The compound (V) has a polyethylene glycol (PEG) chain between the antibiotic 41 of one terminus thereof and the biotin 42 of the other terminus thereof in its chemical structure. Therefore, since the antibiotic 41 is distanced from the work electrode 121 through a predetermined distance, it is possible to detect the microbe 152 in the liquid sample 151 more easily. As a result, it is possible to improve the detection sensitivity of the micro bio sensor 100 to the microbe 152.

As another constitutional example of the complex functional molecules 4, the complex functional molecules 4 may be compound (VII) represented by the following chemical structural formula.

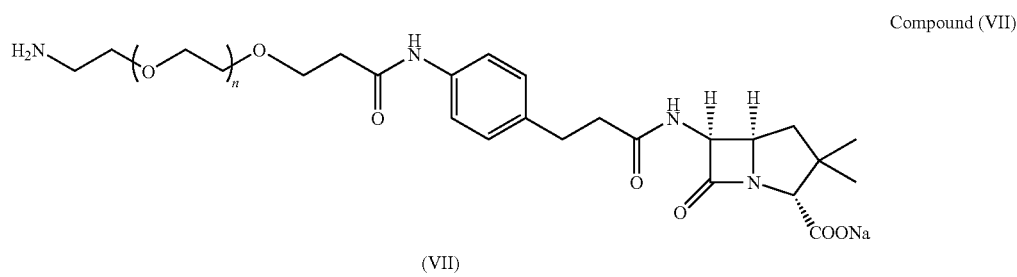

Compound (VII)

(VII)

In the chemical structural formula of the compound (VII), n represents 1 to 15.

In the case where the compound (III) or (IV) is used as the organic molecules 21 in the self-assembled monolayer 2 and the compound (VII) is used as the complex functional molecules 4, an amino group of the compound (VII) can be easily reacted with the carboxyl group of the compound (III) or succinimides of the compound (IV). Therefore, it is possible to easily immobilize the compound (VII), namely the complex functional molecules 4, to the surface of the work electrode 121 through the streptavidins 3 and the self-assembled monolayer 2.

In this regard, it is to be noted that a group to be bonded to the antibiotic 41 in each of the complex functional molecules 4 is not limited to the amide group, and it may be a carboxyl group, an ether group, an ester group or a thioester group. The group is appropriately selected depending on a kind of antibiotic 41 contained in the complex functional molecules 4.

In the present invention, a polymerizable group may be contained in the complex functional molecules 4. Examples of such a polymerizable group include an acrylic group, a methacrylic group and the like. Since such a polymerizable group has a carbon-carbon double bond, it is possible to bond various compounds such as a functional substance having ferrocene and the like to the polymerizable group. This makes it possible for the micro bio sensor 100 to exhibit various functions corresponding to the various compounds such as the functional substance in accordance with the intended use.

For instance, if an antibiotic being different from the antibiotic 41 is bonded to the polymerizable group contained in the complex functional molecules 4, a large number of antibiotics as well as the antibiotic 41 are contained in the complex functional molecules 4 due to polymerization of the polymerizable group. Therefore, it is possible to bond the microbe 152 to the large number of antibiotics as well as the antibiotic 41. As a result, it is possible to improve detection sensitivity of the micro bio sensor 100 to the microbe 152.

As described above, the reaction layer 1 constituted as shown in FIG. 4 makes it possible to exhibit effects described above. Further, in the case where the antibiotic 41 is constituted of the penicillin V of the antimicrobial agent, the penicillin V contained in the reaction layer 1 is bonded to the cell wall of the bacterium and worked on the transpeptidase and the carboxypeptidase which are produced by the bacterium.

And therefore, when a voltage is applied between the work electrode 121 and the opposite electrode 122, an electrical current flowing between the work electrode 121 and the opposite electrode 122 is changed by the bonding between the penicillin V and the cell wall of the bacterium. Further, even if various bacteria are contained in the liquid sample 151, the electrical current is also changed by the same phenomenon as described above.

As a result, it is possible to detect the various bacteria simultaneously. Further, it is also possible to improve detection sensitivity of the micro bio sensor 100 due to the antibiotic 41 contained in the reaction layer 1 of the micro bio sensor 100.

In the reaction layer 1 of the present embodiment, each sulfide group of the compound (I) is bonded to the surface of the work electrode 121 as shown in FIG. 4. Further, the compound (I) is bonded between the organic molecules 21 each having biotin 22 at the upper end thereof (compound (II)) in the self-assembled monolayer 2 of the reaction layer 1 as shown in FIG. 4.

In this way, an appropriate space is formed between adjacent organic molecules 21 each having biotin 22 in the self-assembled monolayer 2. Therefore, even if two complex functional molecules 4 are bonded to one streptavidin 3 as shown in FIG. 4, since adjacent streptavidins 3 are distanced each other due to the space, it is possible to prevent or lower steric hindrance between the complex functional molecules 4 bonded to each of the adjacent streptavidins 3. As a result, it is possible for the antibiotic 41 to exhibit functions thereof reliably, thereby bonding to the microbe 152.

In this regard, it is preferred that a mediator (intermediary agent) which transfers electron to the work electrode 121 as described later is contained in the reaction layer 1. Such a mediator makes it possible to transfer the electron from the reaction layer 1 to the work electrode 121 efficiently. Therefore, it is possible for the micro bio sensor 100 to measure electrical current with high sensitivity.

Examples of such a mediator include potassium ferricyanide, ferrocene, a ferrocene derivative, dicyclopentadienyl nickel, a dicyclopentadienyl nickel derivative, pyridine, a pyridine derivative, quinone, a quinone derivative such as p-benzoquinone, pyrrolo-quinoline quinone and the like, a flavine derivative such as flavin adenine dinucleotide (FAD) and the like, a nicotinamide derivative such as nicotinamide adenine dinucleotide (NAD), nicotinamide adenine dinucleotide phosphate (NADP) and the like, phenazine methosulfate, 2,6-dichlorophenolindophenol, hexacyanoferrate (III), octacyanotungsten ion, a porphyrin derivative, a phthalocyanine derivative and the like. These mediators may be used singly or in combination of two or more of them.

2 Method for Manufacturing Micro Bio Sensor

Hereinbelow, a method for manufacturing the micro bio sensor shown in FIG. 3 according to the invention will be described in details.

Each of FIGS. 5A to 5F and FIGS. 6A and 6B is a view (vertical sectional view) which explains a method for manufacturing the micro bio sensor shown in FIGS. 2 and 3.

In the following description, the upper side in FIGS. 5A to 5F and FIGS. 6A and 6B will be referred to as "upper" and the lower side thereof will be referred to as "lower".

The method for manufacturing the micro bio sensor 100 according to the present embodiment include (2-1) synthesizing complex functional molecules 4, (2-2) forming a work electrode 121, an opposite electrode 122, a reference electrode 123 and wires 130 on a base 120, (2-3) forming an insulation film 160 on an area of the base 120 other than a detection section 110 which is constituted from the work electrode 121, the opposite electrode 122 and the reference electrode 123, and (2-4) forming a reaction layer 1 on the work electrode 121. Hereinbelow, each of these steps (2-1) to (2-4) will be described one after another.

2-1 Step of Synthesizing Complex Functional Molecules (First Step)

2-1-1 First, an antibiotic 41 and a compound containing biotin are prepared to react them.

A concentration of such an antibiotic 41 is preferably in the range of 0.1 to 10 mol/L, and more preferably in the range of 0.5 to 5 mol/L.

A concentration of such a compound containing biotin is preferably in the range of 0.1 to 10 mol/L, and more preferably in the range of 0.5 to 5 mol/L.

If both the concentrations of the antibiotic 41 and the concentration of the compound containing biotin fall within above noted range, the antibiotic 41 is reacted with the compound containing biotin in a just enough quantity. Therefore, it is possible to obtain the complex functional molecules 4 efficiently.

2-1-2 Next, the antibiotic 41 is reacted with the compound containing biotin to obtain the complex functional molecules 4.

A reaction time for reacting the antibiotic 41 and the compound containing biotin is preferably in the range of 0.1 to 10 hours, and more preferably in the range of 0.5 to 3 hours.

A reaction temperature for reacting the antibiotic 41 and the compound containing biotin is preferably in the range of 0 to 80° C., and more preferably in the range of 20 to 60° C.

If each of the reaction time and the reaction temperature for reacting the antibiotic 41 and the compound containing biotin fall within above noted range, the antibiotic 41 is reacted with the compound containing biotin in a just enough quantity. Therefore, it is possible to obtain the complex functional molecules 4 in high yield.

In the present embodiment, the complex functional molecules (biotin-penicillin complex functional molecules) 4 can be obtained by a reaction as represented by the following scheme I.

Scheme I

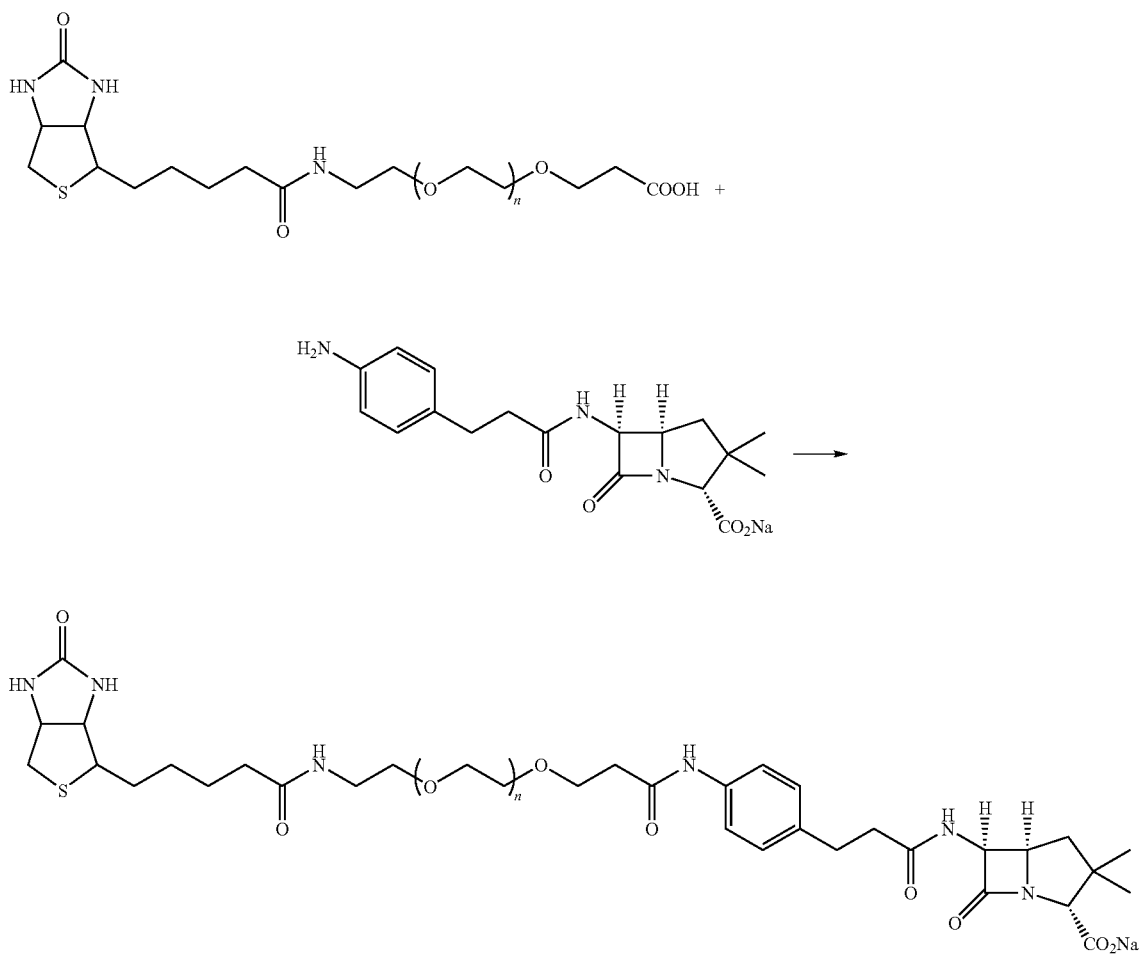

In the scheme I, n represents 1 to 15.

By using such complex functional molecules 4, the biotin 42 contained in the complex functional molecules 4 are easily bonded to streptavidin 3 bonded to the organic molecules (compound (II)) 21 which constitute the self-assembled monolayer 2. Therefore, it is possible to immobilize the antibiotic 41 of the complex functional molecules 4 on the surface of the work electrode 121 through the streptavidin 3 and the self-assembled monolayer 2 easily.

Further, if such complex functional molecules 4 obtained by the reaction as represented by the scheme I are used in the reaction layer 1, the antibiotic 41 is bonded to the surface of the work electrode 121 through at least the biotin 42 and PEG chain as shown in the scheme I. As a result, the antibiotic 41 is distanced from the work electrode 121 so that it is possible to detect a microbe 152 in a liquid sample 151 with high sensitivity.

As another constitutional example of the first step (2-1), complex functional molecules 4 can also be obtained by a reaction as represented by the following scheme II.

Scheme II

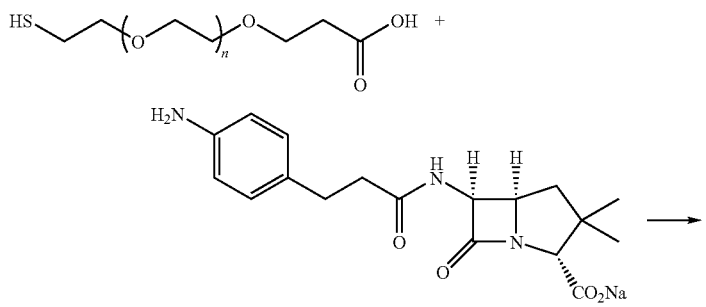

-continued

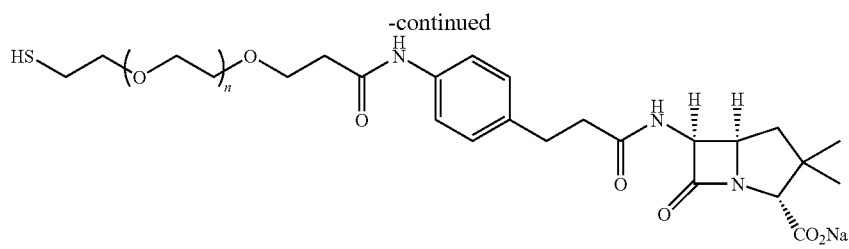

In the scheme II, n represents 1 to 15.

Since no compound containing biotin is used in such a reaction as shown in the scheme II, it is possible to easily obtain a raw material (starting material), namely a carboxylic acid compound to be used in the scheme II. As a result, it is possible to obtain the complex functional molecules 4 as shown in the scheme II easily.

As the other constitutional example of the first step (2-1), complex functional molecules 4 can be also obtained by a reaction as represented by the following scheme III.

Scheme III

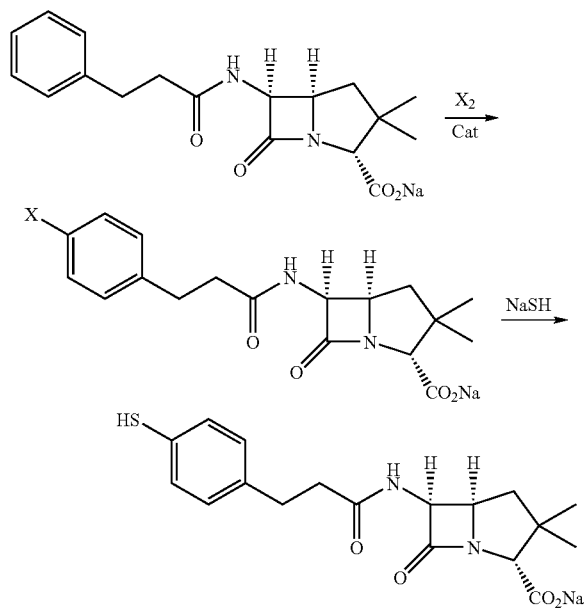

In the scheme III, n represents 1 to 15, X represents halogen such as bromine, chlorine and iodine, and "Cat" represents a catalyst such as iron chloride, iron bromide and copper iodide.

In a complex functional molecule 4 in which a mercapto group is directly bonded at the ortho position of a benzene ring of the penicillin V of the antibiotic 41 to the benzene ring thereof, the complex functional molecule 4 is obtained only by the two steps (halogenations step and displacement reaction step) from the penicillin as shown in the scheme III. Therefore, it is possible to obtain the complex functional molecule 4 by the reaction easier than the reactions which are represented by the schemes I and II.

2-2 Step of Forming Electrodes (Second Step)

Figure 5A:
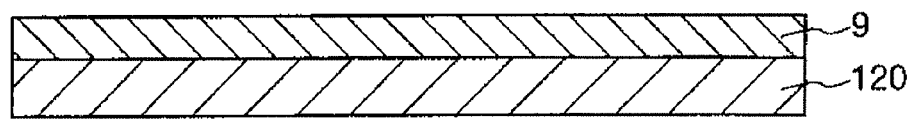
FIGS. 5A to 5F are a view (vertical sectional view) which explains a method for manufacturing the micro bio sensor shown in FIGS. 2 and 3.

2-2-1 First, a base 120 is prepared to form electrodes thereon. And then a metal film (metal layer) 9 is formed on the base 120 as shown in FIG. 5A.

Examples of such a method to form the metal film on the base 120 include: a chemical vapor deposition method (CVD) such as a plasma CVD, a heating CVD and a laser CVD; a vacuum deposition method; a sputtering method (a low temperature sputtering); a dry plating method such as an ion plating; a wet plating method such as an electrolytic plating, a dip plating and an electroless plating; a spray method; a sol-gel method; a MOD method; a junction of a metal foil; and the like.

2-2-2 A resist layer having shapes which correspond to shapes of a work electrode 121, an opposite electrode 122, a reference electrode 123 and wires 130 is formed on a part of the metal film 9 corresponding to the work electrode 121, the opposite electrode 122, the reference electrode 123 and the wires 130 by a photolithography method. And then, the metal film 9 on which no resist layer (unwanted part) is formed is removed by using the resist layer as a mask.

Examples of such a method to remove the metal film 9 (unwanted part) include: a physical etching method such as a plasma etching, a reactive ion etching, a beam etching and a light assist etching; a chemical etching method such as a wet etching; and the like. These methods may be used singly or in combination of two or more of them.

Figure 5B:
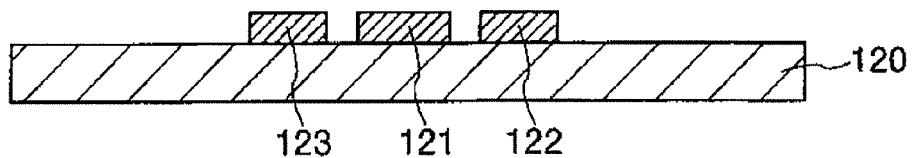

2-2-3 Thereafter, the resist layer formed on the part of the metal film 9 which corresponds to the work electrode 121, the opposite electrode 122, the reference electrode 123 and the wires 130 as shown in FIG. 5B is removed to obtain the work electrode 121, the opposite electrode 122, the reference electrode 123 and the wires 130 (not shown in the drawings).

In this regard, it is to be noted that each of the work electrode 121, the opposite electrode 122, the reference electrode 123 and the wires 130 may also be formed by the following method, respectively. In the other words, a liquid material such as a colloidal liquid containing conductive particles (dispersion liquid) and a liquid containing a conductive polymer (solution or dispersion liquid) is supplied onto the base 120 to form a film of the liquid material.

And then this film is subjected to an after-treatment such as a heating treatment, an infrared irradiation treatment and an ultrasonic treatment if necessary. And thereafter, the formation of the resist layer as described in the step (2-2-2) and the removal of the resist layer as described in the step (2-2-3) are carried out in the same manner to obtain the work electrode 121, the opposite electrode 122, the reference electrode 123 and the wires 130.

Examples of a method for supplying the liquid material onto the base 120 include a dipping method, a spin coating method, a casting method, a micro-gravure coating method, a gravure coating method, a bar coating method, a roll coating method, a wire bar coating method, a dip coating method, a spray coating method, a screen printing method, a flexographic printing method, an offset printing method, an inkjet method, a micro-contact printing method and the like. One or more of these methods may be used independently or in combination.

Among these methods mentioned above, it is preferable to use the inkjet method (a liquid droplet ejecting method). Use of the inkjet method makes it possible to easily form the work electrode 121, the opposite electrode 122, the reference electrode 123 and the wires 130 with increased dimensional accuracy.

2-3 Step of Forming Insulation Film (Third Step)

Figure 5C:
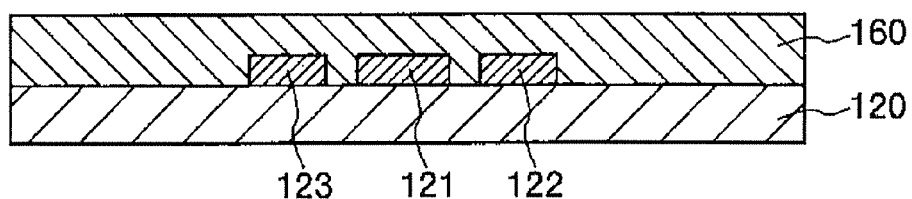
Figure 5D:
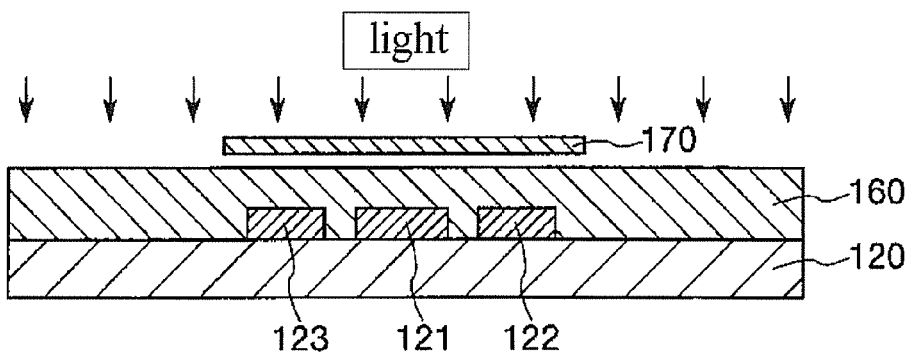
Figure 5E:
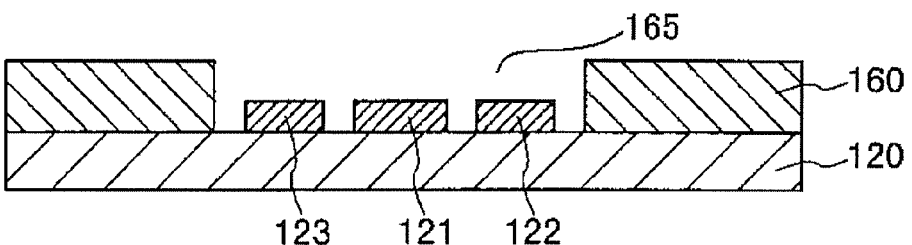

2-3-1 An insulation film 160 having an opening portion 165 in a part thereof which corresponds to a detection section 110 is formed as shown in FIG. 5E.

First, a liquid material containing a predetermined insulation material is prepared. Next, the liquid material is supplied onto the base 120 so as to cover the work electrode 121, the opposite electrode 122, the reference electrode 123 and the wires 130 obtained in the second step (2-2) to obtain the insulation film 160 as shown in FIG. 5C.

In the case where the insulation film 160 is constituted of an inorganic material, the insulation film 160 can be formed by using a thermal oxidation method, a CVD method and a SOG method. Further, use of polysilazane as the inorganic material makes it possible to form a silica film or a silicon nitride film as the insulation film 160 by a wet process.

In the case where the insulation film 160 is constituted of an organic material, a liquid material containing the organic material or precursor thereof is supplied onto the base 120 so as to cover the work electrode 121, the opposite electrode 122, the reference electrode 123 and the wires 130 to obtain a film (insulation film 160). And then, the obtained film may be subjected to an after-treatment such as a heating treatment, an infrared irradiation treatment and an ultrasonic treatment if necessary.

Examples of a method for supplying the liquid material containing the organic material or the precursor thereof onto the base 120 include: a coating method such as a spin coating method and a dip coating method; a printing method such as a screen printing method and an inkjet method; and the like.

In this regard, it is to be noted that an additive such as binder and the like can be added in the liquid material prepared in the present step (2-3-1) if necessary in addition to the insulation material as described above.

2-3-2 Next, a mask 170 is provided on an area of the insulation film 160 to form the detection section 110 as shown in FIG. 5D. And then light is irradiated to the insulation film 160 for patterning. In this way, it is possible to obtain the insulation film 160 as shown in FIG. 5E.

In this regard, it is to be noted that after the light is irradiated to the insulation film 160, the insulation film 160 may be washed by cleaning solution and the like if necessary. This makes it possible to efficiently remove the area of the insulation film 160 (corresponding to the detection section 110) in which the light is blocked by the mask 170.

2-4 Step of Forming Reaction Layer (Fourth Step)

Figure 5F:
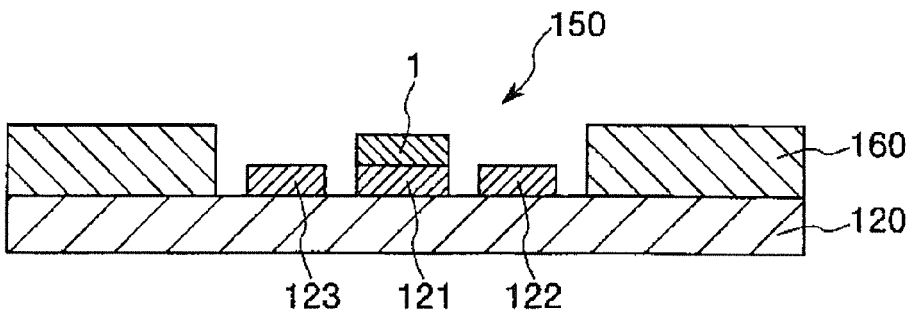

As shown in FIG. 5F, a reaction layer 1 is formed on the work electrode 121.

The present step includes (2-4-1) forming a self-assembled monolayer 2 constituted of organic molecules 21 of which at least one has biotin 22 on the surface of the work electrode 121, (2-4-2) subjecting the self-assembled monolayer 2 to a streptavidin 3 treatment, (2-4-3) immobilizing complex functional molecules 4 to the streptavidin 3 by having the complex functional molecules 4 make contact with the streptavidin 3.

Hereinbelow, each of these steps (2-4-1) to (2-4-3) will be described, respectively.

2-4-1 Step of Forming Self-Assembled Monolayer

In the present step (2-4-1), a method for forming a self-assembled monolayer 2 contained in the reaction layer 1 as shown in FIG. 4 will be described by using an enlarged view shown in FIG. 6A and FIG. 6B.

Figure 6A:
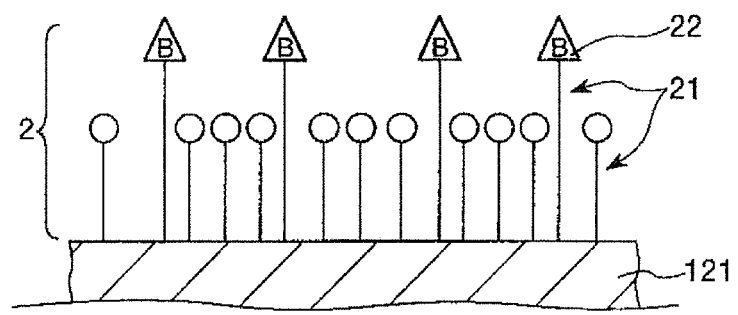
FIGS. 6A and 6B are a view (vertical sectional view) which explains a method for manufacturing the micro bio sensor shown in FIGS. 2 and 3.
Figure 6B:
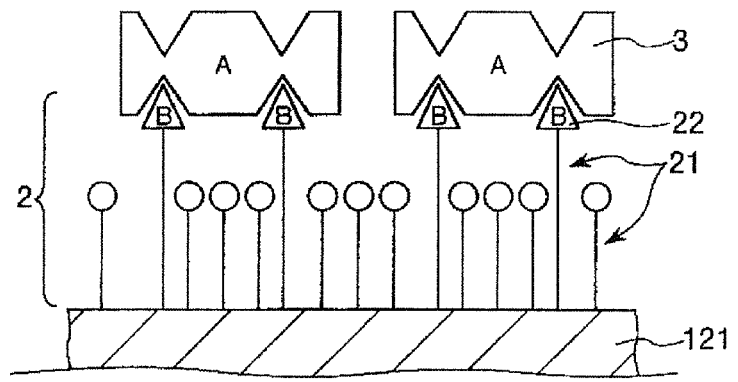

FIG. 6A and FIG. 6B are a schematic view which shows a method for forming the self-assembled monolayer 2 constituting a part of the reaction layer 1 which is provided on the work electrode 121.

First, the organic molecules 21, namely the compounds (I) and (II) as described above are mixed with each other to prepare a liquid material. Next, the prepared liquid material is supplied onto the work electrode 121.

In such a case, an amount ratio between the compounds (I) and (II) is preferably in the range of 9.5:0.5 to 5.5:4.5. If an amount of the compound (I) falls within such a range, the amount of the compound (I) is larger than the amount of the compound (II). Therefore, when both the compounds (I) and (II) are bonded to the surface of the work electrode 121, a larger amount of the compound (I) is bonded to the surface of the work electrode 121 as compared with the compound (II).

Therefore, appropriate spaces are formed between the compounds (II) in the self-assembled monolayer 2 as shown in FIG. 6A due to such an amount ratio described above. Since adjacent compounds (II) are distanced from each other due to the space appropriately, even if two complex functional molecules 4 are bonded to one streptavidin 3 after each biotin 22 of the compounds (II) is subjected to the streptavidin 3 treatment as shown in FIG. 6B, it is possible to prevent or lower steric hindrance between the complex functional molecules 4 bonded to each of the adjacent streptavidins 3. As a result, it is possible to efficiently bond the complex functional molecules 4 to the self-assembled monolayer 2 through the streptavidins 3.

In this regard, it is to be noted that a crosslinking agent may be added in the liquid material if necessary. A concentration (amount) of the compound (II) is set so as to fall in the range of 0.1 to 10 mol/L.

A method for supplying the liquid material containing compounds (II) and (I) onto the surface of the work electrode 121 is carried out by the same method as the method for supplying the liquid material onto the base 120 as described in the second step (2-2-3).

After the liquid material containing compounds (I) and (II) is supplied onto the surface of the work electrode 121, the supplied liquid material is left for a predetermined time. And then, the left liquid material is washed and dried to obtain the self-assembled monolayer 2 constituted of the compounds (I) and (II) having biotin 22 as shown in FIG. 6A.

2-4-2 Step of Subjecting to Streptavidin Treatment

First, a streptavidin 3 solution is prepared through the streptavidin 3 treatment. And then, the self-assembled monolayer 2 obtained in the step (2-4-1) is subjected to the streptavidin 3 treatment. In other words, the streptavidin 3 is bonded (absorbed) to biotin 22 of the compound (II) which constitutes the self-assembled monolayer 2.

The streptavidin 3 solution is prepared by dissolving the streptavidin 3 to a buffer solution. Examples of the buffer solution to dissolve the streptavidin 3 include a Tris buffer solution, a Hepes buffer solution, a phosphate buffer solution, an acetate buffer solution and the like.

A concentration of the streptavidin 3 contained in the streptavidin 3 solution is preferably in the range of 0.05 to 10 mg/ml, and more preferably in the range of 0.1 to 5 mg/ml.

A method for supplying the streptavidin 3 solution to the self-assembled monolayer 2 is carried out by the same method as the method for supplying the liquid material onto the base 120 described in the second step (2-2-3).

After the streptavidin 3 solution is supplied to the self-assembled monolayer 2 to subject the self-assembled monolayer 2 to the streptavidin 3 treatment, the supplied streptavidin 3 solution is left for a predetermined time. And then, the left streptavidin 3 solution is washed and dried. In this way, the streptavidin 3 is bonded (absorb) to the biotin 22 of the compound (II) in the self-assembled monolayer 2 as shown in FIG. 6B.

By subjecting the self-assembled monolayer 2 to the streptavidin 3 treatment, the streptavidin 3 is firmly bonded to the biotin 22 of the compound (II) constituting the self-assembled monolayer 2 with the same bonding strength as that of a covalent bond. Therefore, it is possible to firmly bond the biotin 22 of the compound (II) constituting the self-assembled monolayer 2 to the streptavidin 3 on the lower side thereof.

Further, by subjecting the self-assembled monolayer 2 to the streptavidin 3 treatment, one streptavidin 3 is bonded to four biotins. Therefore, two biotins 42 of the complex functional molecules 4 can further be bonded to the streptavidin 3 on the upper side thereof.

In other words, one streptavidin 3 is bonded to the two biotins 22 of the two compounds (II) (organic molecules 21) on the lower side thereof and the two biotins 42 of the two complex functional molecules 4 on the upper side thereof as shown in FIG. 4.

Therefore, since the two complex functional molecules 4 are bonded to the streptavidin 3, it is possible to immobilize the many complex functional molecules 4 containing the antibiotic 41 on the surface of the work electrode 121 through the self-assembled monolayer 2 and the streptavidin 3. As a result, it is possible to improve detection sensitivity of the micro bio sensor 100 to the microbe 152.

2-4-3 Step of Immobilizing Complex Functional Molecules

The complex functional molecules 4 obtained by the first step (2-1) are supplied to the self-assembled monolayer 2 (one side of the work electrode 121) which has been subjected to the streptavidin 3 treatment in the step (2-4-2).

A method for supplying the complex functional molecules 4 to the self-assembled monolayer 2 which has been subjected to the streptavidin 3 treatment is carried out by the same method as the method for supplying the liquid material onto the base 120 described in the second step (2-2-3).

A concentration of the complex functional molecules 4 supplied to the self-assembled monolayer 2 which has been subjected to the streptavidin 3 treatment is preferably in the range of 0.1 to 10 mol/L, and more preferably in the range of 0.5 to 8 mol/L.

The supplied complex functional molecules 4 are left for a predetermined time. And then, the left complex functional molecules 4 are washed and dried to obtain the micro bio sensor 100 as shown in FIG. 3 and FIG. 4.

This makes it possible to obtain the micro bio sensor 100 in which the antibiotic 41 of the complex functional molecules 4 is immobilized on the surface of the work electrode 121 through the streptavidin 3 and the self-assembled monolayer 2.

As another constitutional example of the present step (2-4-3), the complex functional molecules 4 obtained by the reaction as represented by the scheme II of the first step (2-1-2) are supplied onto the surface of the work electrode 121 directly, so that it is also possible to immobilize the complex functional molecules 4 on the surface of the work electrode 121. In this case, since each mercapto group of the complex functional molecules 4 is bonded to the surface of the work electrode 121 directly, it is possible to easily and rapidly immobilize the antibiotic 41 of the complex functional molecules 4 on the surface of the work electrode 121.

As the other constitutional example of the present step (2-4-3), the complex functional molecules 4 obtained by the reaction as represented by the scheme III of the first step (2-1-2) are supplied onto the surface of the work electrode 121 directly, so that it is also possible to immobilize the complex functional molecules 4 on the surface of the work electrode 121 directly.

In this case, the antibiotic 41 (penicillin V) of the complex functional molecules 4 is bonded to the surface of the work electrode 121 through a sulfur atom which is bonded at the ortho position of the benzene ring of the complex functional molecules 4 (penicillin V) to the benzene ring thereof. Therefore, it is possible to immobilize the penicillin V on the surface of the work electrode 121 in an excellent orientation, and therefore it is possible to detect the microbe 152 with high sensitivity.

By the steps as described above, it is possible to obtain the micro bio sensor 100 as shown in FIG. 4. The micro bio sensor 100 can be used in various fields to detect the microbe 152. Examples of such various fields include a medical field, a food field, a medicine field, a cosmetic field and the like.

3 Operation of Micro Bio Sensor

Next, a description will be made with regard to operation of the micro bio sensor 100 as shown in FIG. 1 according to the invention.

First, the liquid sample 151 containing the microbe 152 is supplied to the sample supply space 150 of the micro bio sensor 100 of the present invention as shown in FIG. 3 and FIG. 4.

When the liquid sample 151 containing a microbe 152 is supplied to the sample supply space 150, the liquid sample 151 is in contact with the reaction layer 1 of the micro bio sensor 100. In a state that the liquid sample 151 is in contact with the reaction layer 1, the antibiotic 41 existing in an upper surface of the reaction layer 1 works to enzymes which are served in a peptidoglycan biosynthesis of the cell wall of the microbe 152 contained in the liquid sample 151. And then the antibiotic 41 prevents the peptidoglycan from forming cross-rinks as described above. Thereafter, the antibiotic 41 is reacted with the cell wall (cell surface 5) and is bonded to the cell surface 5.

At this time, a voltage is applied between the work electrode 121 and the opposite electrode 122 so that a predetermined alternating current (AC) flows between the work electrode 121 and the opposite electrode 122. In this case, if a microbe 152 exists in the liquid sample 151, the bonding between the microbe 152 and the antibiotic 41 in the reaction layer 1 gives some influences to the properties of the work electrode 121 through the self-assembled monolayer 2 (namely, through the complex functional molecules 4, the biotins 42, the streptavidins 3, the biotins 22 and the organic molecules 21).

As a result, the impedance of the alternating current flowing between the work electrode 121 and the opposite electrode 122 is changed due to the bonding between the microbe 152 and the antibiotic 41 in the reaction layer 1. In other words, the impedance of the alternating current flowing between the work electrode 121 and the opposite electrode 122 is changed depending on the cases whether or not any microbe 152 exists in the liquid sample 151 and the microbe 152 is bonded to the antibiotic 41. As a result, it is possible to detect presence of the microbe 152 in the liquid sample 151 based on the change of the impedance.

In the case where a concentration of the microbe 152 contained in the liquid sample 151 is examined, namely in case of a quantitative analysis of the microbe 152, the quantitative analysis is carried out as follows. First, liquid samples 151 containing the microbe 152 having predetermined different concentrations (reference liquid samples) are prepared.

And then each reference liquid samples is examined by the micro bio sensor 150 of the present invention so that the microbe 152 contained in each liquid sample 151 is detected to measure impedance of the electrical current flowing between the work electrode 121 and the opposite electrode 122.

Thereafter, a calibration curve is plotted using a graph in which the ordinate axis represents the impedance of the alternating current measured in each of the reference liquid samples and the abscissa axis represents the concentration of the microbe 152 in each of the reference liquid samples.

Next, a liquid sample 151 containing the microbe 152 of unknown concentration (real sample) is examined by the micro bio sensor 152 as described above so that the microbe 152 contained in the real sample is detected to measure impedance of the alternating current flowing between the work electrode 121 and the opposite electrode 122. Thereafter, the concentration of the microbe 152 contained in the real sample can be obtained by using the measured impedance and the calibration curve.

According to the method described above, it is possible to detect presence or absence of the microbe 152 in the liquid sample 151 and it is also possible to determine quantity or concentration of the microbe 152 in the liquid sample 151.

Second Embodiment

Figure 7:
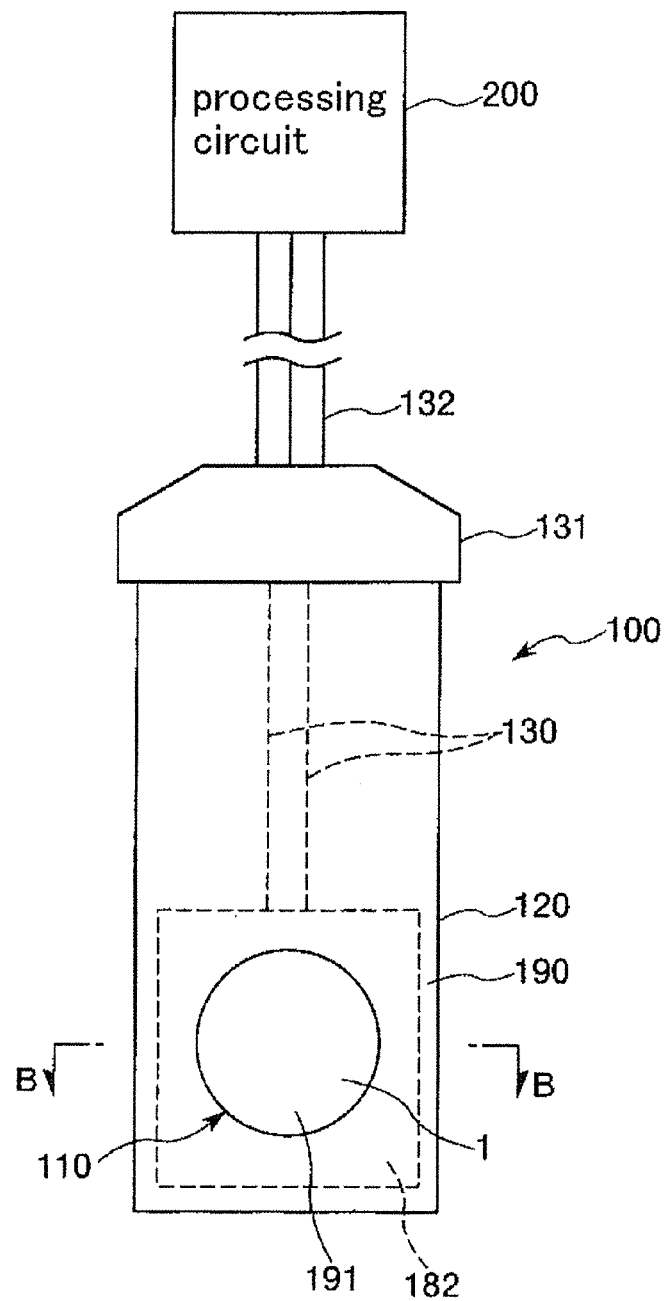
FIG. 7 is a plan view which schematically shows a second embodiment of a micro bio sensor in accordance with the present invention.
Figure 8:
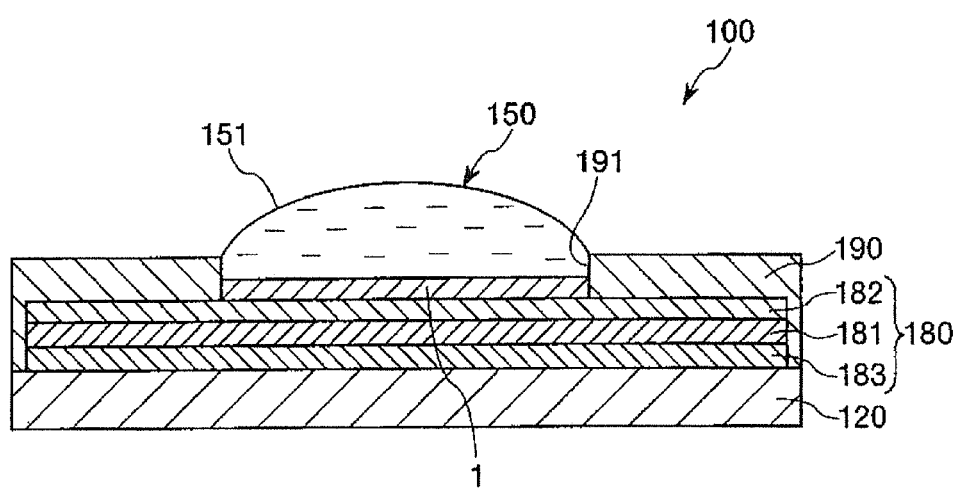
FIG. 8 is a vertical sectional view taken along line B-B in FIG. 7, which shows the micro bio sensor shown in FIG. 7.

FIG. 7 is a plan view which schematically shows a second embodiment of the micro bio sensor shown in FIG. 1. FIG. 8 is a vertical sectional view taken along line B-B in FIG. 7, which shows the micro bio sensor shown in FIG. 7.

In the following description, the front side of the sheet of FIG. 7 will be referred to as "upper" and the back side thereof will be referred to as "lower". Further, the upper side in FIG. 8 will be referred to as "upper" and the lower side thereof will be referred to as "lower".

Hereinbelow, a description will be made with regard to a micro bio sensor of a second embodiment and a method for manufacturing the micro bio sensor according to the invention. The description of the second embodiment will be focused on the points differing from the micro bio sensor of the first embodiment, and steps of the method for manufacturing the micro bio sensor of the second embodiment which are common with the first embodiment are omitted.

1 Micro Bio Sensor

A micro bio sensor 100 shown in FIG. 7 includes a crystal oscillator (detector) 180 provided on a base 120 and an outer flame (housing) 190 provided on the base 120 so as to protect the detector 180 as shown in FIG. 7 and FIG. 8. The detector 180 is composed from a piezoelectric layer 181 constituted of crystal and a pair of electrodes 182 and 183 between which the piezoelectric layer 181 is provided. Each of the electrodes 182 and 183 is electrically connected to a processing circuit 200 through wires 130 and 132.

In this regard, it is to be noted that the processing circuit 200 functions as a oscillation circuit and has a function of counting a frequency of a signal which is generated by the detector 180.

As shown in FIG. 8, a surface of the detector 180 other than a detection section 110 is covered with the housing 190. The housing 190 has an opening portion 191. A surface of the electrode 182 corresponding to the detection section 110 is exposed in the opening portion 191. A reaction layer 1 is formed on the exposed surface of the electrode 182, thereby constituting the detection section 110.

A frequency of the signal generated by the detector 180 is preferably in the range of 3 to 30 MHz, and more preferably in the range of 9 to 27 MHz.

2 Method for Manufacturing Micro Bio Sensor

Hereinbelow, a method for manufacturing the micro bio sensor according to the present embodiment will be described.

First, an electrode 183 and wires 130 are formed at a predetermined position of a base 120 by the same method as the method described in the Step of Forming Electrodes (2-2) of the first embodiment shown in FIG. 5A and FIG. 5B.

Next, a crystal plate (piezoelectric layer 181) is provided on the electrode 183 and then an electrode 182 is formed on the piezoelectric layer 181 by the same method as the method described in the Step of Forming Electrodes (2-2) of the first embodiment to obtain a detector 180.

Next, a housing 190 is provided on the base 120 so as to cover the wires 130 and a part of the detector 180 other than a part of the electrode 182 corresponding to a detection section 110. Finally, a reaction layer 1 is formed on the surface of the electrode 182 exposed in the opening portion 191 by the same method as the method described in the Step of Forming Reaction Layer (2-4) of the first embodiment to obtain the micro bio sensor 100 as shown in FIG. 7 and FIG. 8.

3 Operation of Micro Bio Sensor

Next, a description will be made with regard to operation of the micro bio sensor 100 shown in FIG. 7 and FIG. 8 according to the invention.

In such a micro bio sensor 100 shown in FIG. 7 and FIG. 8, if the liquid sample 151 containing the microbe 152 is supplied to the sample supply space 150 partitioned (defined) by the base 120 and the housing 190, the reaction layer 1 formed on the electrode 181 is in contact with the liquid sample 151.

If the liquid sample 151 is in contact with the reaction layer 1, the antibiotic 41 existing at an upper surface of the reaction layer 1 works to enzymes which are served in the peptidoglycan biosynthesis of the cell wall of the microbe 152 contained in the liquid sample 151. And then the antibiotic 41 prevents the peptidoglycan from forming cross-rinks as described above. Thereafter, the antibiotic 41 is reacted with the cell wall (cell surface 5) and is bonded to the cell surface 5.

At this time, if the voltage is applied between the electrodes 182 and 183, weight of the reaction layer 1 is changed by the bonding between the microbe 152 and the antibiotic 41 which is contained in the reaction layer 1. Therefore, a vibrational frequency of the signal generated by the detector 180 is also changed by the bonding between the microbe 152 and the antibiotic 41.

The processing circuit 200 carries out a predetermined processing based on the detection results, namely the vibrational frequency of the signal generated by the detector 180 in a state that no microbe 152 is bonded to the antibiotic 42 and the vibrational frequency changed by the bonding between the microbe 152 and the antibiotic 41. Then, a frequency of the changed vibrational frequency is calculated by the processing circuit 200.

In this way, it is possible to detect the microbe 152 contained in the liquid sample 151 based on the changed vibrational frequency due to the weight of the reaction layer 1 which is changed by the bonding between the microbe 152 and the antibiotic 41.

As described above, use of the detector 180 for detecting the microbe 152 contained in the liquid sample 151 makes it possible to omit some steps such as the step of forming the self-assembled monolayer used in the first embodiment. As a result, it is possible to obtain the micro bio sensor 100 easily and rapidly.

Although the micro bio sensor and the method for manufacturing the micro bio sensor of the present invention have been described with reference to the illustrated embodiments, the present invention is not limited thereto. The configuration of each component may possibly be replaced by other arbitrary configurations having equivalent functions. It may also be possible to add other optional components to the present invention.

Further, the micro bio sensor of the present invention may have a structure that can be obtained by combining the respective embodiments described above.

Hereinbelow, although experimental examples of the present invention will be described in detail, the present invention is not limited thereto.

EXAMPLES

Example 1

1 Manufacturing of Micro Bio Sensor 1-1 First, 1 mmol of a compound in which an amino group was bonded at the ortho position of a benzene ring of a penicillin V to the benzene ring thereof and 1 mmol of Biotin PEG acid (37141-1195, produced by Polypure As) were prepared, respectively.

DCC (dicyclohexylcarbodiimide) was mixed with anhydrous DMF to obtain a mixture of 20 mL. The compound, the Biotin PEG acid and the mixture were added in a vessel and then were reacted for 10 hours at a temperature of 50° C. with stirring as shown in the follow scheme IV to obtain precipitate. Thereafter, the thus obtained precipitate was filtered, washed by DMF, and then dried in vacuum to obtain a biotin-penicillin complex functional molecule.

Scheme IV

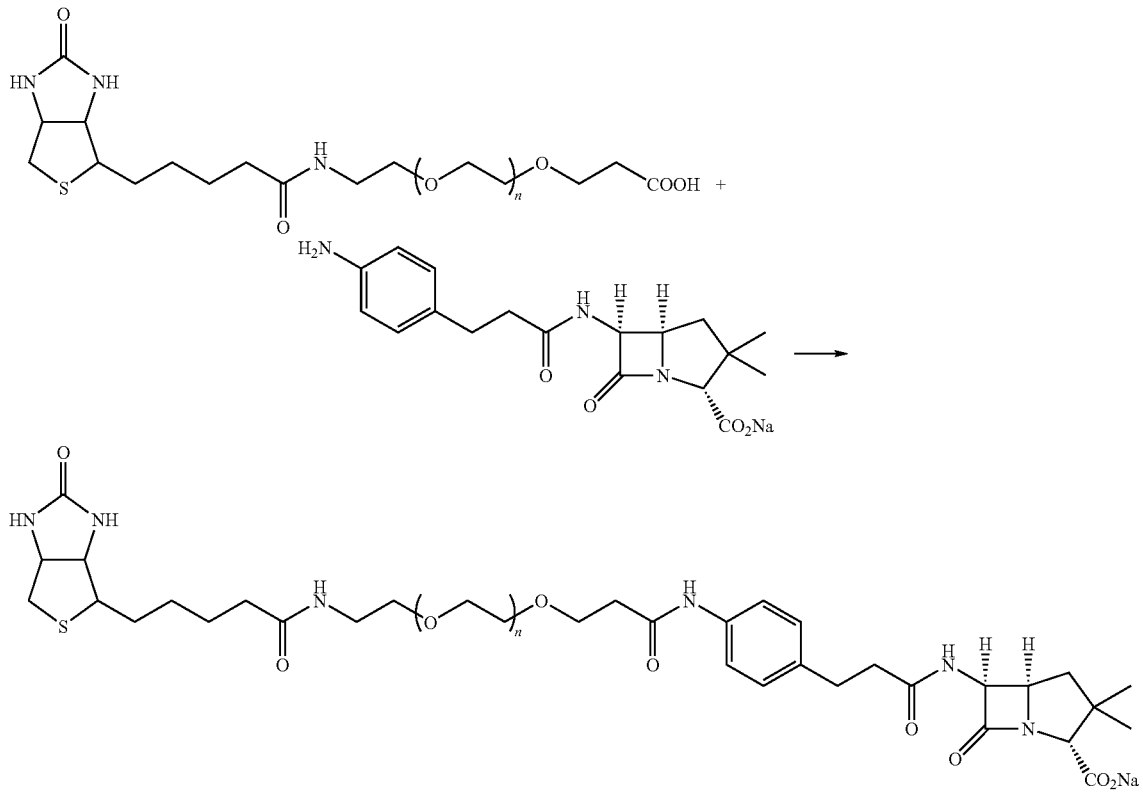

In the Scheme IV, n represents 11.

1-2 Next, a base made of a resin was prepared. Then, gold was deposited on the base by a vacuum deposition method to obtain a gold film. Next, a resist layer having shapes which respectively correspond to shapes of a work electrode, an opposite electrode, a reference electrode and wires was formed on parts of the gold film to form the work electrode, the opposite electrode, the reference electrode and the wires by a photolithography method.

And then the gold film on which no resist layer was formed (unwanted part) was removed by a plasma etching method using the resist layer as a mask. Thereafter, the resist layer was removed to obtain the work electrode, the opposite electrode, the reference electrode and the wires provided on the base.

1-3 Next, silicon dioxide was supplied onto the base so as to cover the work electrode, the opposite electrode, the reference electrode and the wires to obtain a layer having a thickness of 400 nm. A mask was set on an area of the layer to form a detection section, and then light was irradiated to the surface of the layer to obtain an insulation film.

1-4 Next, a compound (I) represented by the following chemical formula (11156-0695, produced by Polypure As) and a compound (VIII) represented by the following chemical formula (41151-0895, produced by Polypure AS) were added in anhydrous ethanol of 1 mmol/L at a mixing ratio of 9:1. And then the compounds (I) and (VIII) were dissolved in the anhydrous ethanol to obtain a mixture of 1 mmol/L.

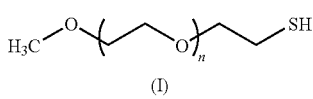

Compound I

In the chemical formula of the compound (I), n represents 6.

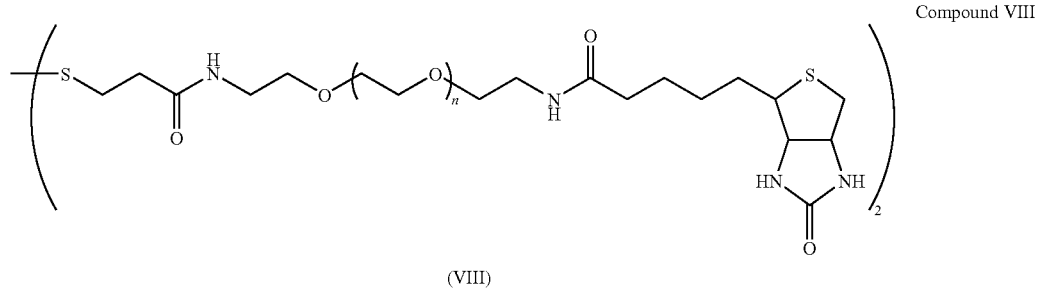

Compound VIII

In the chemical formula of the compound (VIII), n represents 8.

The mixture was supplied onto the surface of the work electrode constituted of the gold, and thereafter the supplied mixture was washed by anhydrous ethanol and then dried by nitrogen to obtain a self-assembled monolayer constituted of the compounds (I) and (VIII).

1-5 Next, Tris buffer solution of 30 μL, which has a concentration of 50 mmol/L, was supplied to the self-assembled monolayer. Then, 10 μL (0.25 mg/mL) of a streptavidin solution having a concentration of 1 mg/mL was added in the Tris buffer solution supplied to the self-assembled monolayer, which was left for 1 hour. After the leaving, Tris buffer solution in which the streptavidin solution was added was washed by anhydrous ethanol and dried by nitrogen to obtain a self-assembled monolayer which was subjected to a streptavidin treatment.

1-6 The biotin-penicillin complex functional molecule obtained in the step (1-1) was supplied to the self-assembled monolayer which was subjected to the streptavidin treatment in the step (1-5). After leaving for 1 hour, the supplied biotin-penicillin complex functional molecule was washed and dried to obtain a micro bio sensor in which the penicillin V was immobilized on the surface of the work electrode through the self-assembled monolayer contained in the reaction layer.

Example 2

In Example 1, a micro bio sensor was manufactured in the same manner as in the Example 1 except that the Biotin PEG acid was changed to PEG thiol acid (37156-0795, produced by Polypure As) and the PEG thiol was directly supplied onto the surface of the work electrode constituted of gold.

Example 3

In Example 1, a micro bio sensor was manufactured in the same manner as in the Example 1 except that the biotin-penicillin complex functional molecule was changed to penicillin V thiol and the penicillin V thiol was directly supplied onto the surface of the work electrode constituted of gold.

2 Evaluation 2-1 A liquid sample was prepared by diluting a test strain of lactic acid bacterium so that an amount of the lactic acid bacterium was in the range of 0.01 to 1.0 CFU/ml. Further, a blank sample in which no lactic acid bacterium was contained was also prepared.

2-2 Next, a voltage was applied between the work electrode and the opposite electrode so that a predetermined alternating current (AC) flows between the work electrode and the opposite electrode. Then, the liquid sample and the blank sample were supplied to the detection section of each of the micro bio sensors obtained in Examples 1 to 3 to be in contact with the lactic acid bacterium contained in the liquid sample and the penicillin V contained in the reaction layer, respectively.

Thereafter, in each micro bio sensor obtained in Examples 1 to 3, impedance of alternating current flowing between the work electrode and the opposite electrode was measured in each of the liquid sample and the blank sample. Then, the impedance of the alternating current flowing between the work electrode and the opposite electrode in the case of using the liquid sample was compared with the impedance of the alternating current flowing between the work electrode and the opposite electrode in the case of using the blank sample. Thus compared impedance was evaluated.

As a result, in the case of using the liquid sample, the impedance of the alternating current flowing between the work electrode and the opposite electrode is changed due to the bonding between the lactic acid bacterium and the penicillin V in the reaction layer. In other words, the impedance of the alternating current flowing between the work electrode and the opposite electrode is changed depending on the cases whether or not the lactic acid bacterium exists in the liquid sample and the lactic acid bacterium is bonded to the penicillin V. As a result, it is possible to detect presence of the lactic acid bacterium in the liquid sample based on the change of the impedance.

As a result, in each micro bio sensor obtained in Examples 1 to 3, the impedance in the case of using the liquid sample was changed for about 20% in the impedance as compared with the case using the blank sample. In this way, it is recognized that the lactic acid bacterium is bonded to the penicillin V. Therefore, since it is possible for the micro bio sensor according to the present invention to detect a microbe with high sensitivity easily and rapidly, it is possible to make great contribution to related industries.

What is claimed is:

1. A micro bio sensor which detects a microbe existing in a specimen, the micro bio sensor comprising:

a detector disposed on a base, the detector including a first electrode; and a reaction layer disposed on the detector, and the microbe being detected by the detector due to bonding between the reaction layer and the microbe, the reaction layer including:

a self-assembled monolayer which includes a plurality of molecules, each of the plurality of molecules having one end and an other end, the one end bonding with the first electrode;

a first biotin which is disposed at the other end of at least one of the plurality of molecules;

streptavidin which is bonded with the first biotin; and a complex functional molecule which includes a second biotin, a polyethylene glycol chain and a penicillin antibiotic, an amide bonding being located between the second biotin and the polyethylene glycol chain and between the penicillin antibiotic and the polyethylene glycol chain, the second biotin being bonded with the streptavidin.

to the bonding between the penicillin antibiotic and the microbe.

4. The micro bio sensor as claimed in claim 1, wherein the detector is comprised of the first electrode, a second electrode and a piezoelectric layer formed between the first electrode and the second electrode, and the detector is configured to oscillate in a predetermined frequency.

5. The micro bio sensor as claimed in claim 4, wherein the microbe is detected by the detector in a state that a voltage is applied between the first electrode and the second electrode, wherein when the microbe existing in the specimen is bonded to the penicillin antibiotic contained in the reaction layer, the predetermined frequency is changed due to the bonding between the penicillin antibiotic and the microbe.

6. The micro bio sensor as claimed in claim 1, the detector further including a second electrode and a third electrode.

7. The micro bio sensor as claimed in claim 1, the complex functional molecule represented by the following formula, where n represents 1 to 15.

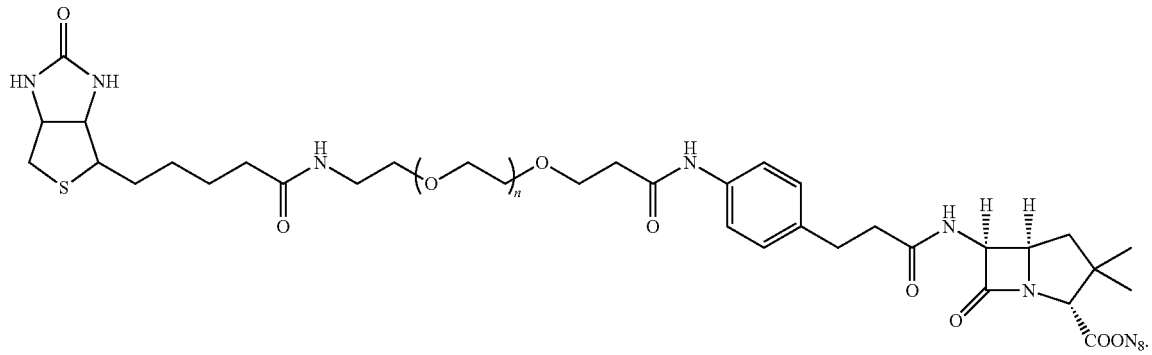

2. The micro bio sensor as claimed in claim 1, wherein the complex functional molecule contains a polymerizable group.

8. The micro bio sensor as claimed in claim 7, each of the plurality of molecules being represented by the following formula (I) or (II), where n represents 1 to 15

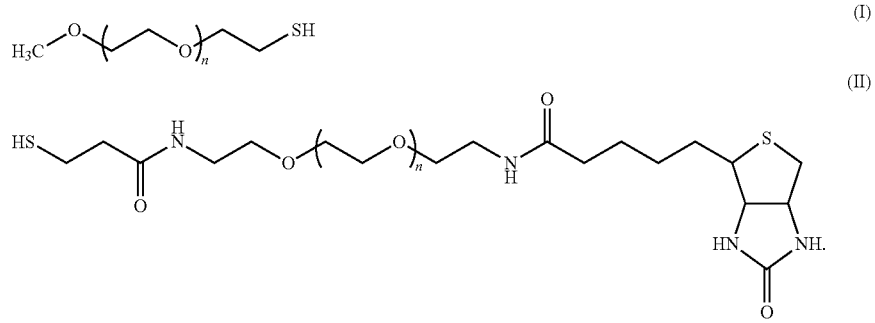

3. The micro bio sensor as claimed in claim 1, wherein the detector further includes a second electrode arranged in a side by side relation the first electrode, and the microbe is detected by the first and second electrodes in a state that a voltage is applied between the first electrode and the second electrode to obtain an impedance of an electrical current flowing between the first and second electrodes, wherein when the microbe existing in the specimen is bonded to the penicillin antibiotic contained in the reaction layer, the impedance is changed due 9. A method for manufacturing a micro bio sensor, the method comprising:

forming a detector on a base; and forming a reaction layer on the detector, and a microbe being detected by the detector due to bonding between the reaction layer and the microbe;

the forming of the reaction layer on the detector including:

preparing a complex functional molecule which includes a second biotin, a polyethylene glycol chain and a penicillin antibiotic, an amide bonding being located between the second biotin and the polyethylene glycol chain and between the penicillin antibiotic and the polyethylene glycol chain;

forming a self-assembled monolayer which includes a plurality of molecules, each of the plurality of molecules having one end and an other end, a first biotin being disposed at the other end of at least one of the plurality of molecules;

performing steptavidin treatment to bond a steptavidin to the first biotin; and immobilizing the complex functional molecules to bond the second biotin to the streptavidin.

10. A micro bio sensor which detects a microbe existing in a specimen, the micro bio sensor comprising:

a detector disposed on a base, the detector including a first electrode; and a reaction layer disposed on the detector, and the microbe being detected by the detector due to bonding between the reaction layer and the microbe, the reaction layer including:
   a self-assembled monolayer which includes a plurality of molecules, each of the plurality of molecules having one end and the other end, the one end bonding with the first electrode;
   a first biotin which is disposed at the other end of at least one of the plurality of molecules;
   streptavidin which is bonded with the first biotin; and
   a complex functional molecule which includes a second biotin, a polyethylene glycol chain and an antibiotic;

wherein the second biotin is bonded to the antibiotic through the polyethylene glycol chain, and the second biotin is bonded with the streptavidin.

* * * * *